(12) United States Patent
Yen et al.

(10) Patent No.: US 11,111,244 B2
(45) Date of Patent: Sep. 7, 2021

(54) ORGANIC COMPOUND AND ORGANIC ELECTROLUMINESCENCE DEVICE USING THE SAME

(71) Applicants: Feng-Wen Yen, Taipei (TW); Shu-Hua Yeh, Hsinchu (TW)

(72) Inventors: Feng-Wen Yen, Taipei (TW); Shu-Hua Yeh, Hsinchu (TW)

(73) Assignee: LUMINESCENCE TECHNOLOGY CORP., Hsin-Chu (TW)

( * ) Notice: Subject to any disclaimer, the term of this patent is extended or adjusted under 35 U.S.C. 154(b) by 375 days.

(21) Appl. No.: 16/153,853

(22) Filed: Oct. 8, 2018

(65) Prior Publication Data

US 2020/0109138 A1 Apr. 9, 2020

(51) Int. Cl.
| | | |
|---|---|---|
| *H01L 51/50* | (2006.01) | |
| *C07D 471/04* | (2006.01) | |
| *C07D 241/46* | (2006.01) | |
| *C07D 307/91* | (2006.01) | |
| *C07D 405/04* | (2006.01) | |
| *C07D 405/12* | (2006.01) | |
| *C07D 403/04* | (2006.01) | |
| *C07C 211/61* | (2006.01) | |
| *H01L 51/00* | (2006.01) | |
| *C07D 251/24* | (2006.01) | |
| *H01L 51/52* | (2006.01) | |

(52) U.S. Cl.
CPC ........ *C07D 471/04* (2013.01); *C07C 211/61* (2013.01); *C07D 241/46* (2013.01); *C07D 251/24* (2013.01); *C07D 307/91* (2013.01); *C07D 403/04* (2013.01); *C07D 405/04* (2013.01); *C07D 405/12* (2013.01); *H01L 51/006* (2013.01); *H01L 51/0058* (2013.01); *H01L 51/0067* (2013.01); *H01L 51/0072* (2013.01); *H01L 51/0073* (2013.01); *H01L 51/0074* (2013.01); *H01L 51/5012* (2013.01); *H01L 51/5076* (2013.01); *H01L 51/5206* (2013.01); *H01L 51/5221* (2013.01)

(58) Field of Classification Search
None
See application file for complete search history.

(56) References Cited

U.S. PATENT DOCUMENTS

| | | | |
|---|---|---|---|
| 2006/0244698 A1* | 11/2006 | Koshimizu | G09G 3/3637 345/80 |
| 2008/0111473 A1* | 5/2008 | Kawamura | C07D 239/26 313/504 |
| 2018/0155325 A1 | 6/2018 | Lee et al. | |

FOREIGN PATENT DOCUMENTS

| | | | | |
|---|---|---|---|---|
| KR | 2017-69724 | * | 6/2017 | ............ H01L 51/50 |
| WO | 2017109722 A1 | | 6/2017 | |

\* cited by examiner

*Primary Examiner* — Gregory D Clark

(57) ABSTRACT

An organic compound which can be used as the phosphorescent host material, the fluorescent host material, or the fluorescent dopant material of the light emitting layer, and/or the electron transporting material of the organic electroluminescence device is disclosed. The organic electroluminescence device employing the organic compound can lower driving voltage, prolong half-lifetime, and increase current efficiency.

11 Claims, 1 Drawing Sheet

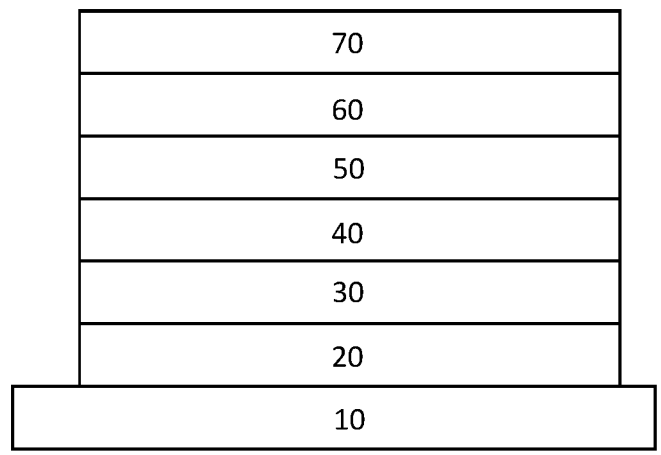

ORGANIC COMPOUND AND ORGANIC ELECTROLUMINESCENCE DEVICE USING THE SAME

FIELD OF INVENTION

The present invention relates to a novel organic compound and, more particularly, to an organic electroluminescence device using the organic compound.

BACKGROUND OF THE INVENTION

An organic electroluminescence (organic EL) device is an organic light-emitting diode (OLED) in which the light emitting layer is a film made from organic compounds, which emits light in response to the electric current. The light emitting layer containing the organic compound is sandwiched between two electrodes. The organic EL device is applied to flat panel displays due to its high illumination, low weight, ultra-thin profile, self-illumination without back light, low power consumption, wide viewing angle, high contrast, simple fabrication methods and rapid response time.

Typically, the organic EL device is composed of organic material layers sandwiched between two electrodes. The organic material layers include, e.g., hole injection layer (HIL), hole transporting layer (HTL), emitting layer (EML), electron transporting layer (ETL), and electron injection layer (EIL). The basic mechanism of organic EL involves the injection, transport, and recombination of carriers as well as exciton formation for emitting light. When an external voltage is applied across the organic EL device, electrons and holes are injected from the cathode and the anode, respectively. Electrons will be injected from the cathode into a LUMO (lowest unoccupied molecular orbital) and holes will be injected from the anode into a HOMO (highest occupied molecular orbital). Subsequently, the electrons recombine with holes in the light emitting layer to form excitons, which then deactivate to emit light. When luminescent molecules absorb energy to achieve an excited state, the exciton may either be in a singlet state or a triplet state, depending on how the spins of the electrons and holes have been combined. It is well known that the excitons formed under electrical excitation typically include 25% singlet excitons and 75% triplet excitons. In the fluorescence materials, however, the electrically generated energy in the 75% triplet excitons will be dissipated as heat for decay from the triplet state is spin forbidden. Therefore, a fluorescent electroluminescence device has only 25% internal quantum efficiency, which leads to the theoretically highest external quantum efficiency (EQE) of only 5% due to only 20% of the light out-coupling efficiency of the device. In contrast to fluorescent electroluminescence devices, phosphorescent organic EL devices make use of spin-orbit interactions to facilitate intersystem crossing between singlet and triplet states, thus obtaining emission from both singlet and triplet states and the internal quantum efficiency of electroluminescence devices from 25% to 100%.

For full-colored flat panel displays using organic EL devices, the organic materials used in the organic EL devices are still unsatisfactory in half-life time, power consumption, luminance, and current efficiency. Therefore, there is still a need for an organic compound that can lower the driving voltage, increase the current efficiency and luminance, and prolong the half-life time for the organic EL device.

SUMMARY OF THE INVENTION

Accordingly, an object of the invention is to provide a novel organic compound and an organic EL device using the same, which can exhibit improved luminance, current efficiency, and half-life time.

Another object of the invention is to provide a novel organic compound and an organic EL device using the same, which can operate under reduced voltage and exhibit higher current efficiency and longer half-life time.

Still another object of the present invention is to provide an organic compound, which can be used as a phosphorescent host material, a fluorescent host material, or a fluorescent dopant material in the emitting layer, and/or an electron transporting material in an organic EL device to improve the power consumption, luminance, current efficiency, or life time.

According to the present invention, an organic compound which can be used in organic EL devices is disclosed. The organic compound is represented by the following formula (1) or formula (2):

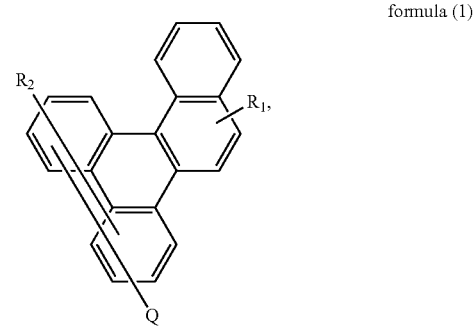

formula (1)

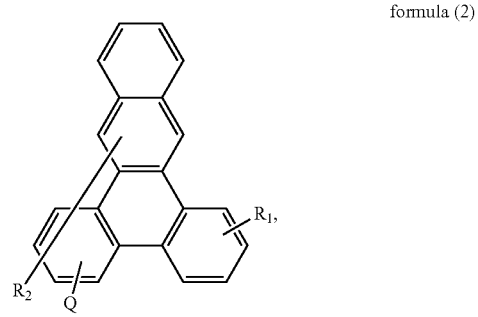

formula (2)

wherein Q is a group represented by formula (3) below:

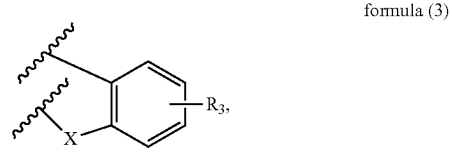

formula (3)

wherein X is a divalent bridge selected from the group consisting of O, S, $NR_4$, $CR_5R_6$, and $SiR_7R_8$; $R_1$ to $R_3$ are independently absent, a hydrogen atom, a halogen, a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms; $R_4$ is a hydrogen atom, a halogen, a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms; and $R_5$ to $R_8$ are independently a hydrogen atom, a halogen, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, or a substituted or unsubstituted heteroaryl group having 3 to 30 carbon atoms.

The present invention further discloses an organic electroluminescence device. The organic electroluminescence device comprises a pair of electrodes composed of a cathode and an anode, and a light emitting layer and one or more organic thin film layers between the pair of electrodes. At least one of the light emitting layer and the organic thin film layer comprises the organic compound of formula (1) or formula (2).

BRIEF DESCRIPTION OF THE DRAWINGS

The FIGURE is a schematic view showing an organic EL device according to an embodiment of the present invention.

DESCRIPTION OF THE PREFERRED EMBODIMENTS

What probed into the invention is the organic compound and organic EL device using the organic compound. Detailed descriptions of the production, structure and elements will be provided as follows such that the invention can be fully understood. Obviously, the application of the invention is not confined to specific details familiar to those skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, an organic compound which can be used as the phosphorescent host material, the fluorescent host material, or the fluorescent dopant material of the light emitting layer, and/or the electron transporting material of the organic EL device is disclosed. The organic compound is represented by the following formula (1) or formula (2):

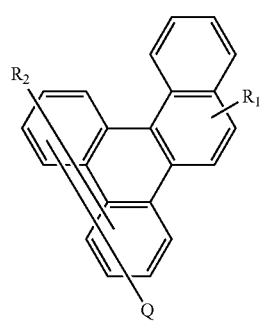

formula (1)

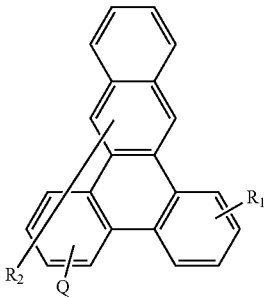

formula (2)

wherein Q is a group represented by formula (3) below:

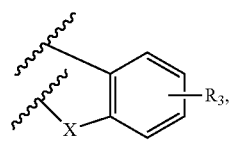

formula (3)

wherein X is a divalent bridge selected from the group consisting of O, S, $NR_4$, $CR_5R_6$, and $SiR_7R_8$; $R_1$ to $R_3$ are independently absent, a hydrogen atom, a halogen, a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms; $R_4$ is a hydrogen atom, a halogen, a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms; and $R_5$ to $R_8$ are independently a hydrogen atom, a halogen, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, or a substituted or unsubstituted heteroaryl group having 3 to 30 carbon atoms.

In some embodiments, the organic compound is represented by one of the following formula (4) to formula (21):

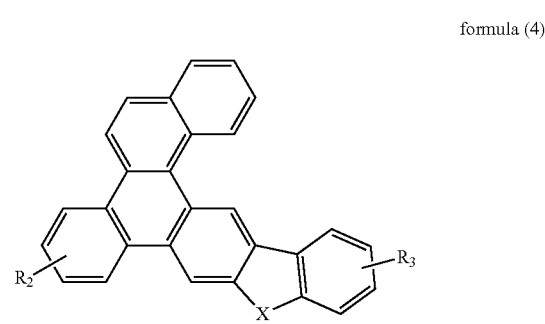

formula (4)

formula (5)
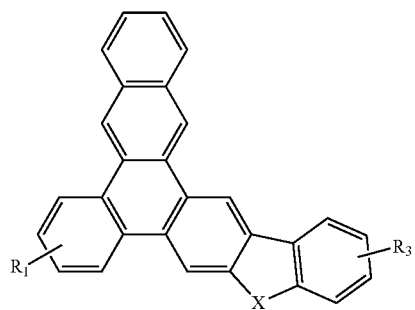
formula (6)
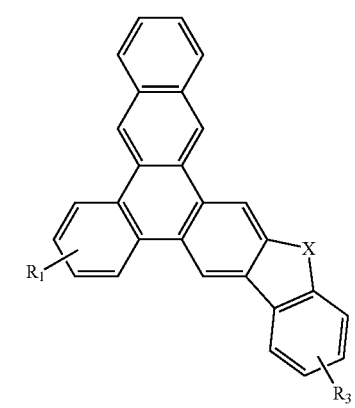
formula (7)
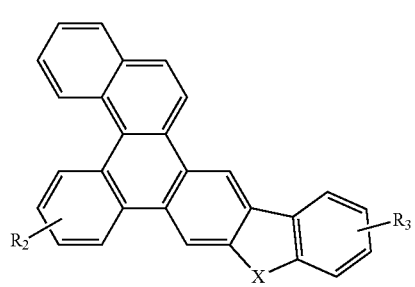
formula (8)
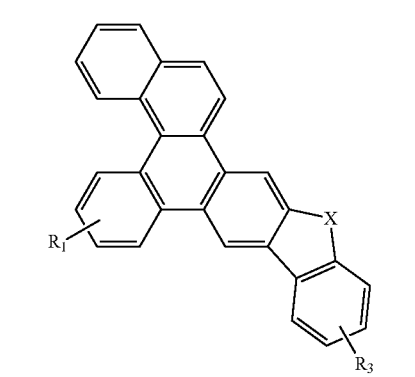
formula (9)
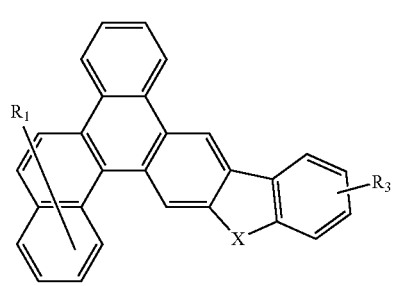
formula (10)
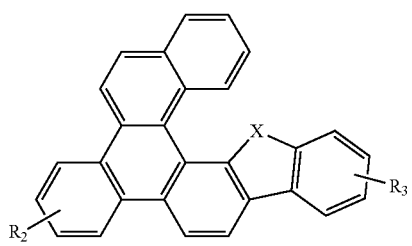
formula (11)
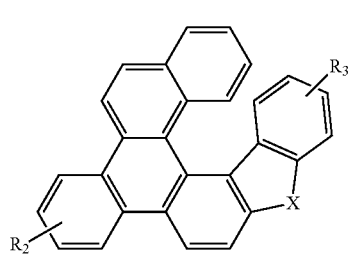
formula (12)
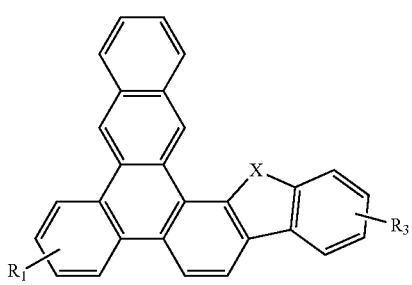
formula (13)
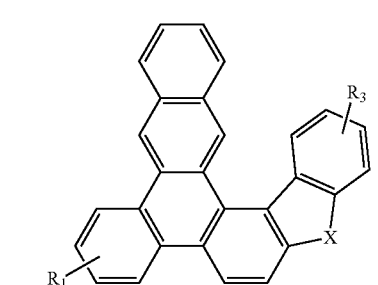
formula (14)
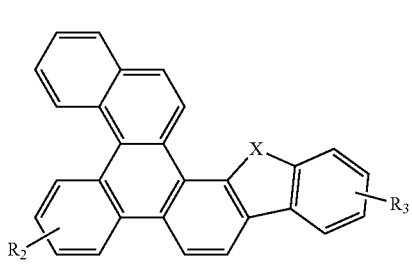
formula (15)
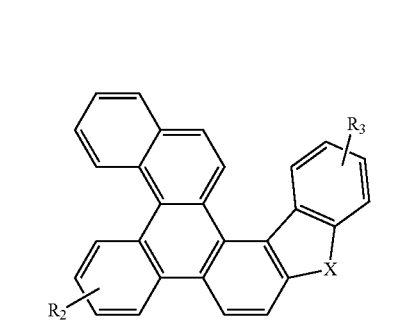

formula (16)
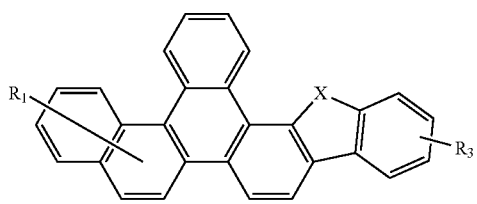

formula (17)
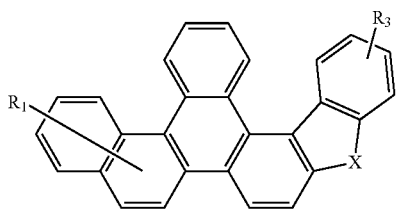

formula (18)
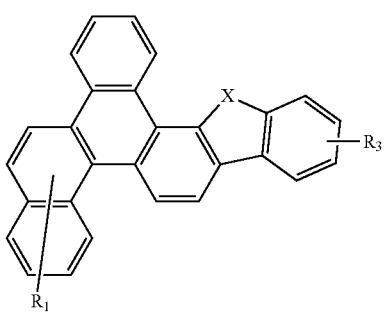

formula (19)
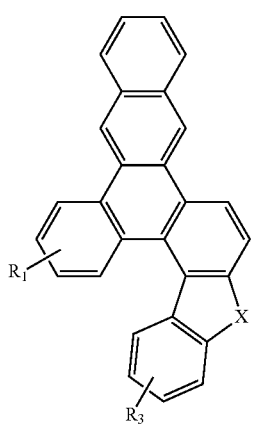

formula (20)
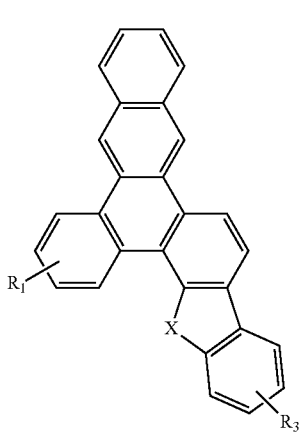

formula (21)
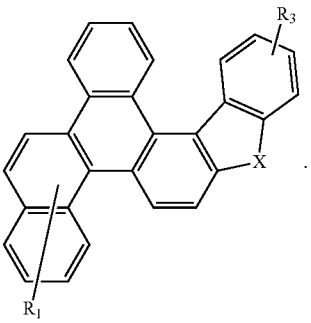

In some embodiments, the alkyl group, aralkyl group, aryl group, heteroaryl group, arylamine group, or heteroarylamine group may be substituted by a halogen, an alkyl group, an aryl group, or a heteroaryl group.

In some embodiments, $R_1$ to $R_4$ are independently a substituted or unsubstituted phenyl group, a substituted or unsubstituted biphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted triphenylenyl group, a substituted or unsubstituted benzimidazole group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted diphenylphosphine oxide group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group, a substituted or unsubstituted dihydrophenazine group, a substituted or unsubstituted diphenylamine group, a substituted or unsubstituted triphenylamine group, a substituted or unsubstituted phenyldibenzofuranylamine group, or a substituted or unsubstituted phenyldibenzothiophenylamine group.

In some embodiments, $R_1$ to $R_4$ independently represent one of the following substituents:

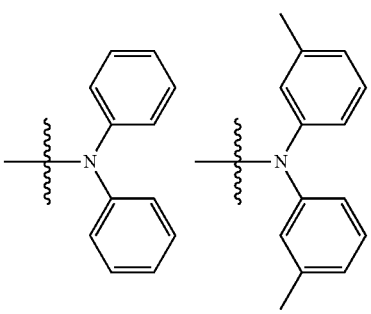

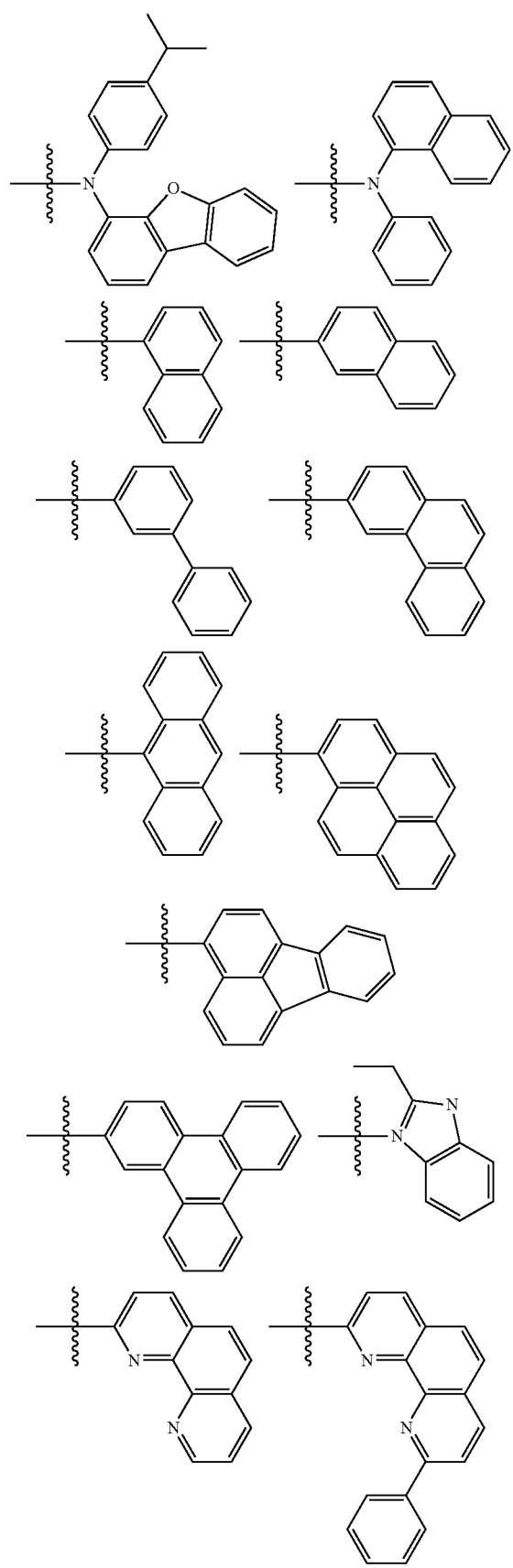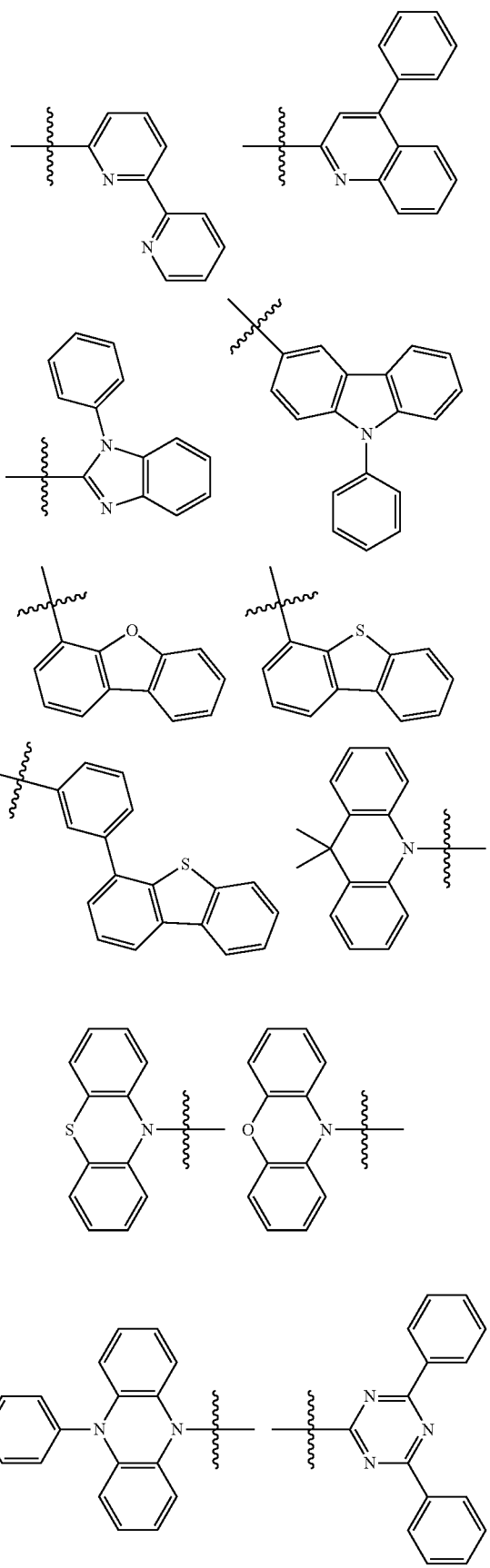

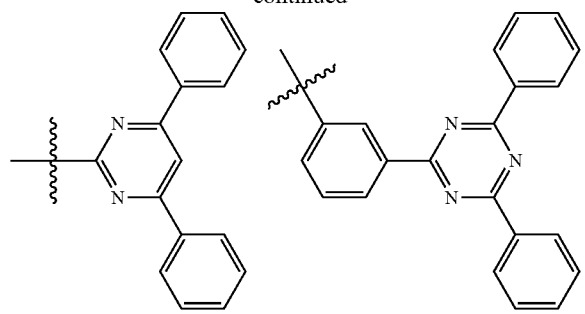
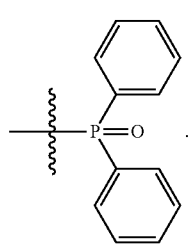
Preferably, the organic compound is one of the following compounds:
C1
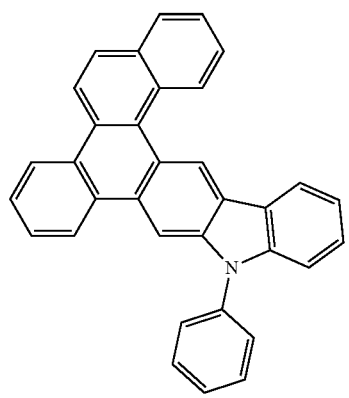
C2
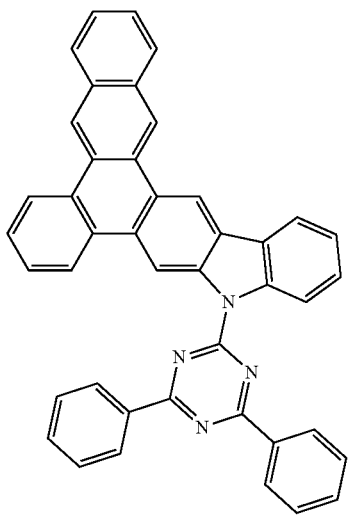
C3
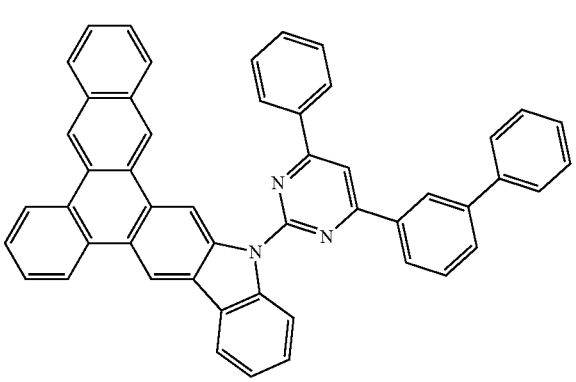
C4
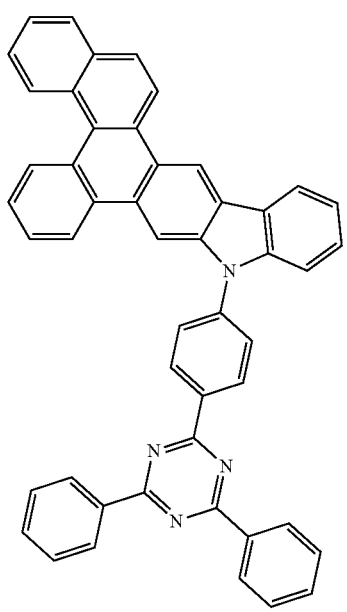
C5
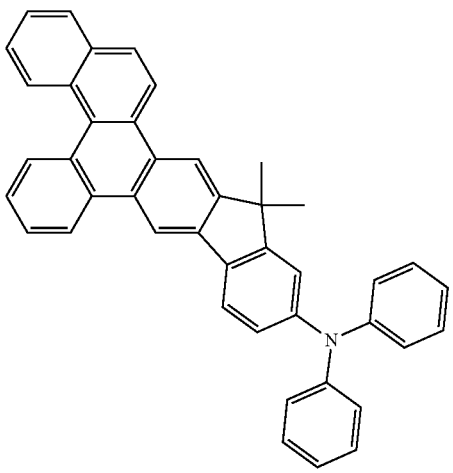

-continued
C6
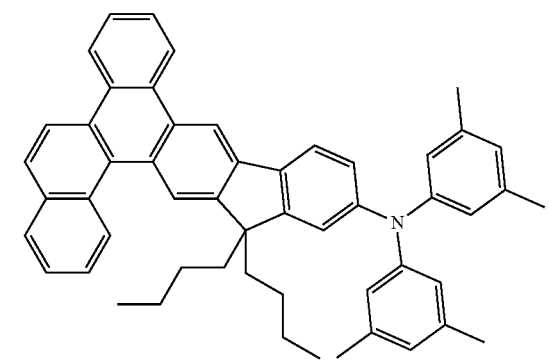
C7
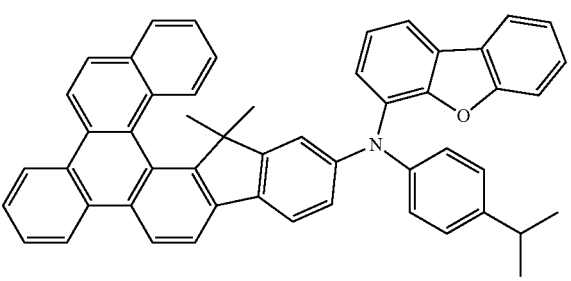
C8
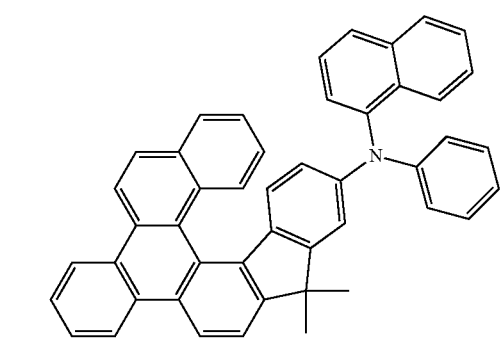
C9
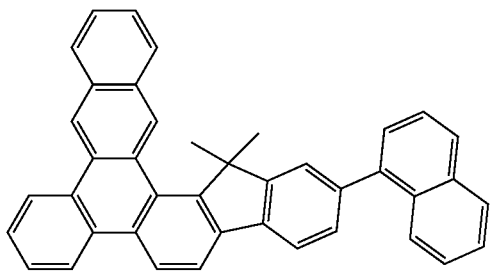
C10
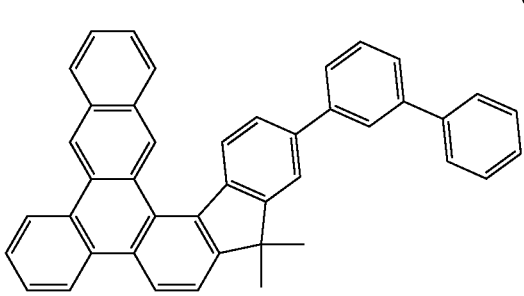
-continued
C11
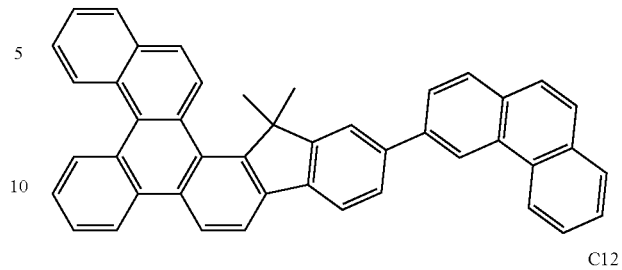
C12
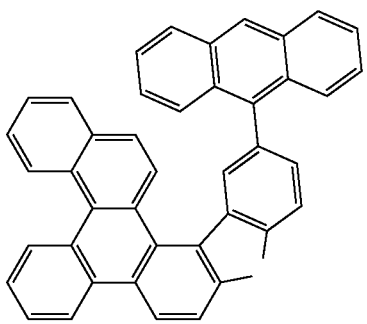
C13
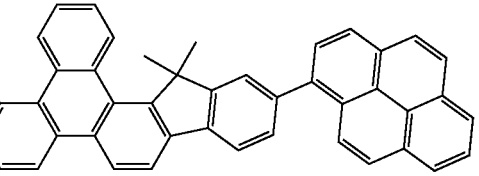
C14
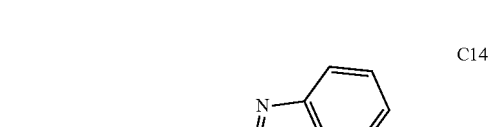
C15
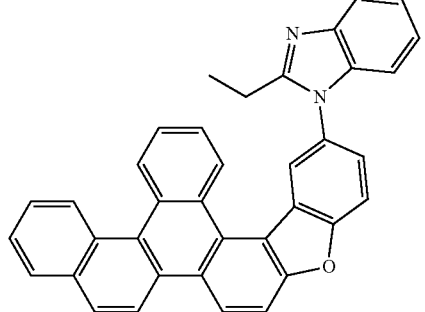

C16
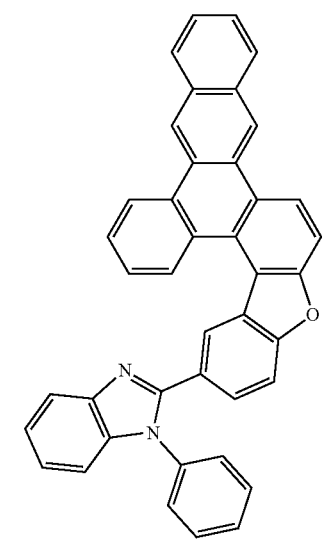
C17
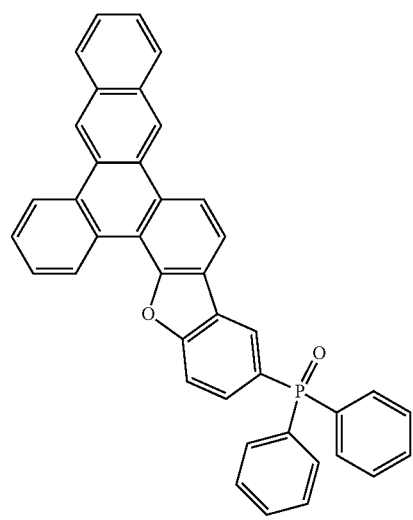
C18
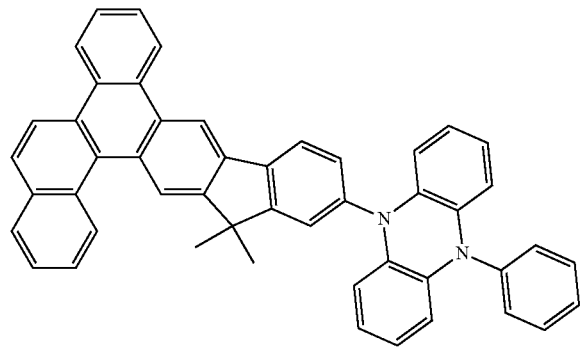
C19
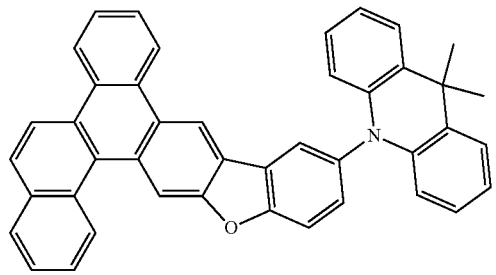
C20
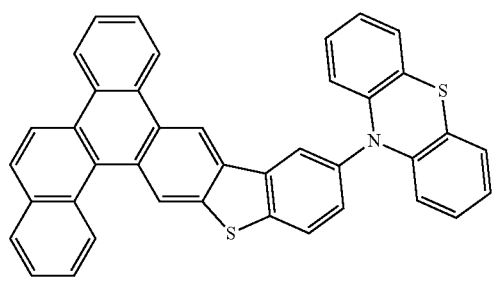
C21
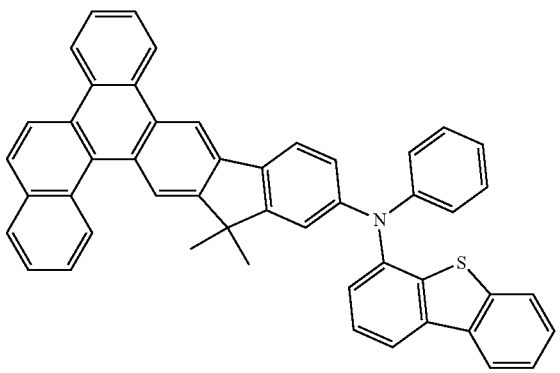
C22
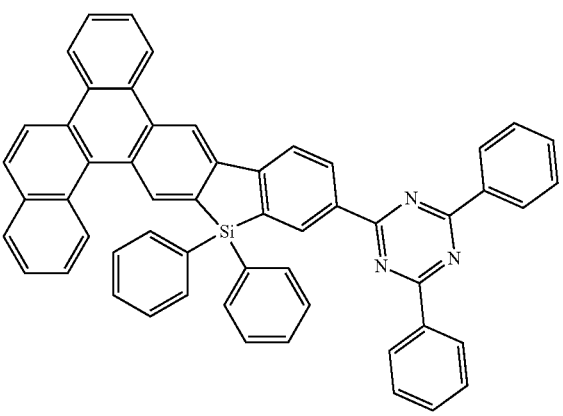

C23
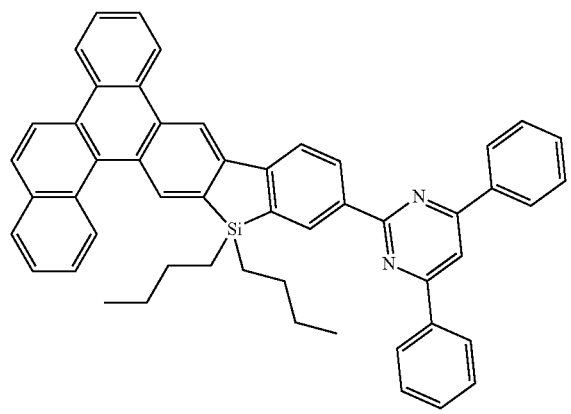
C24
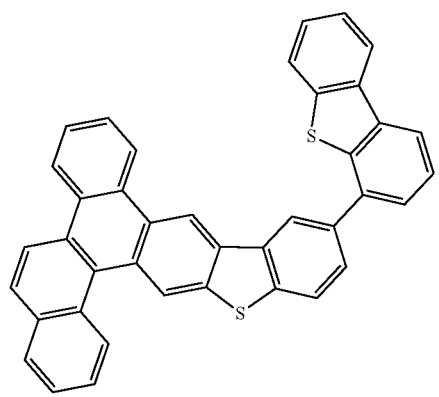
C25
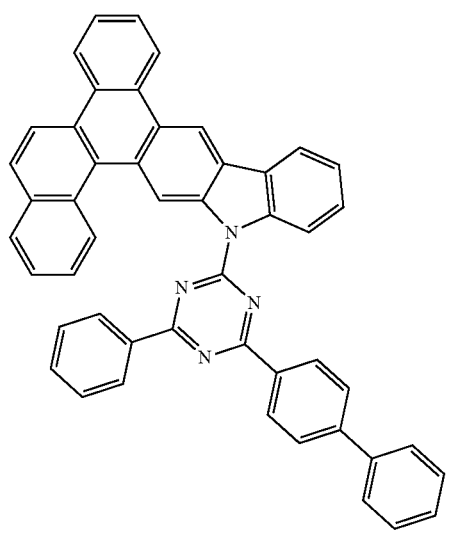
C26
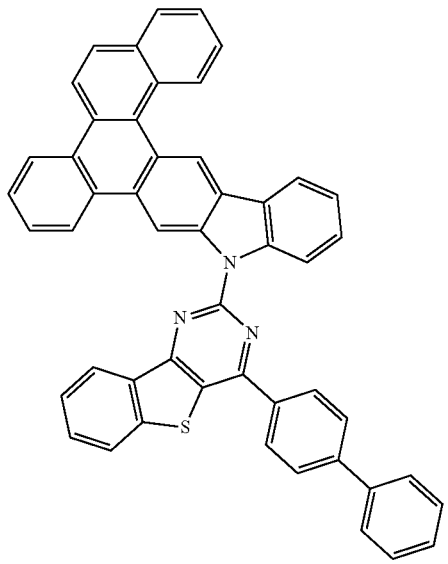
C27
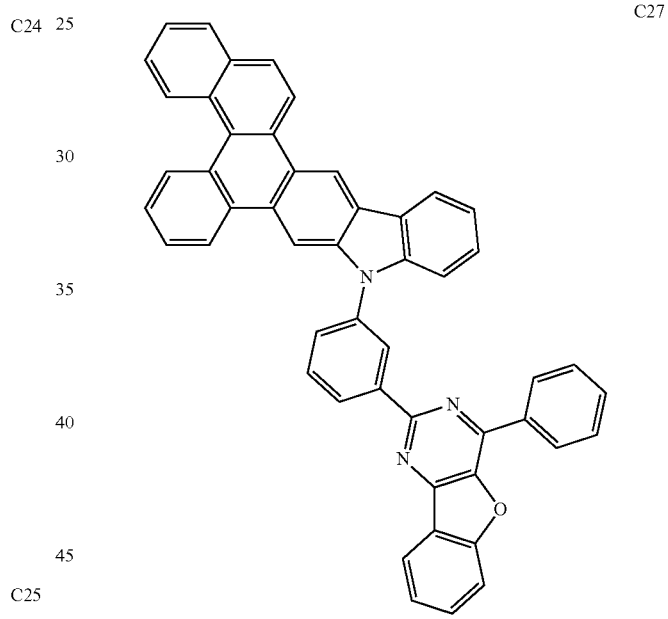
C28
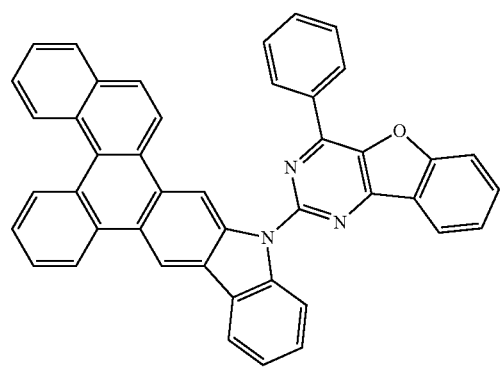

C29
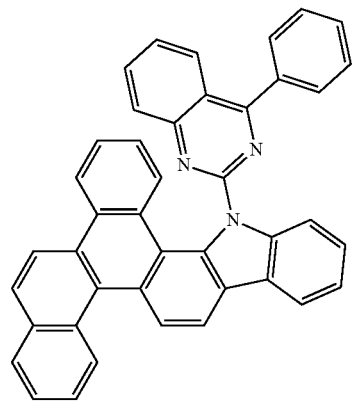
C30
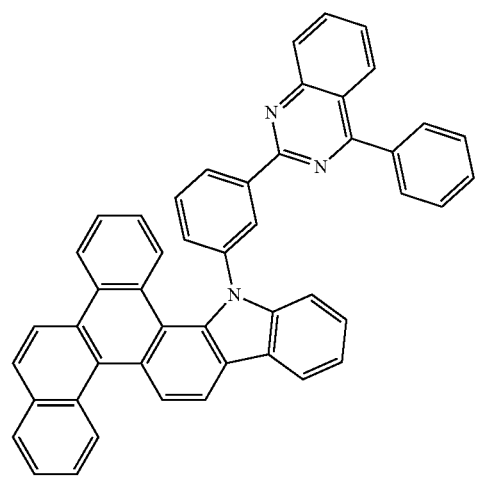
C31
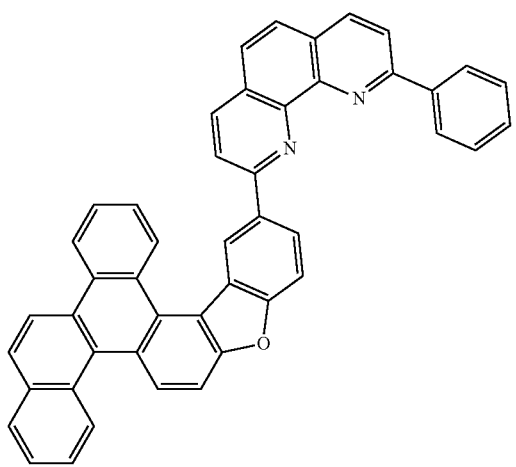
C32
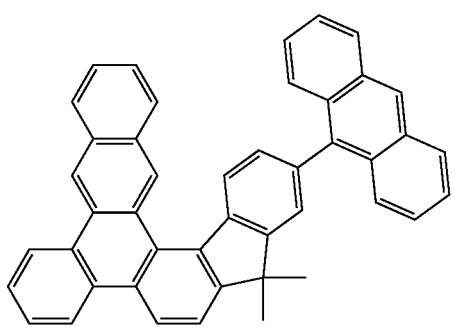
C33
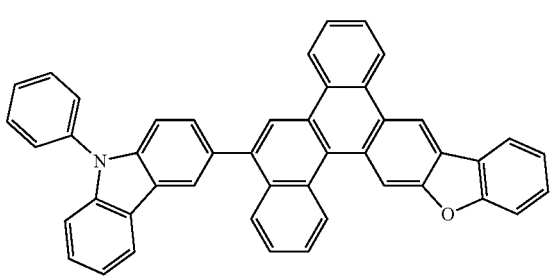
C34
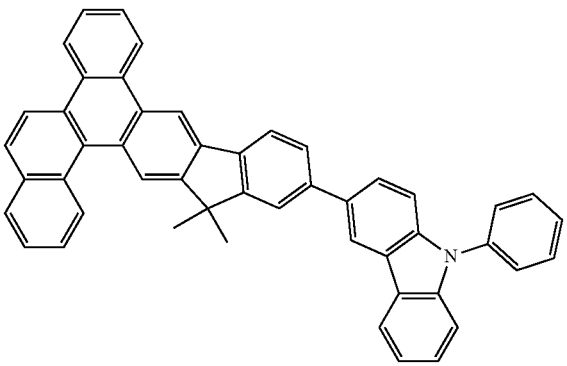
C35
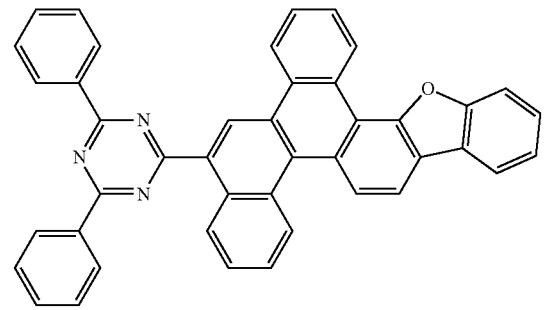

C36
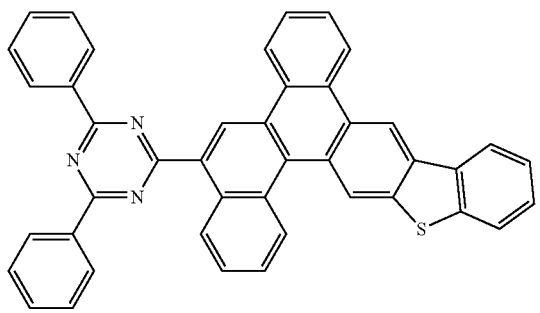
C37
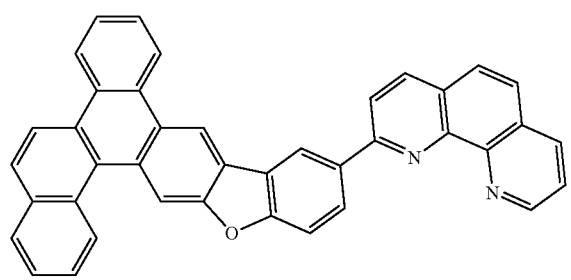
C38
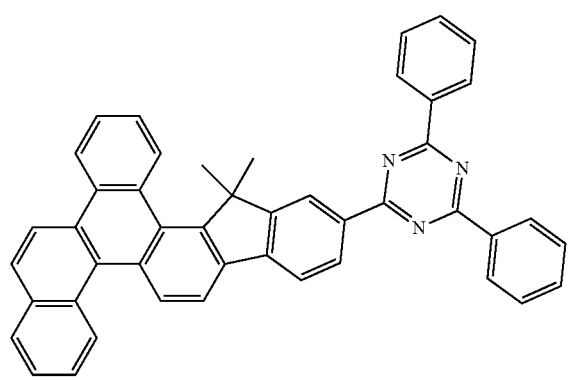
C39
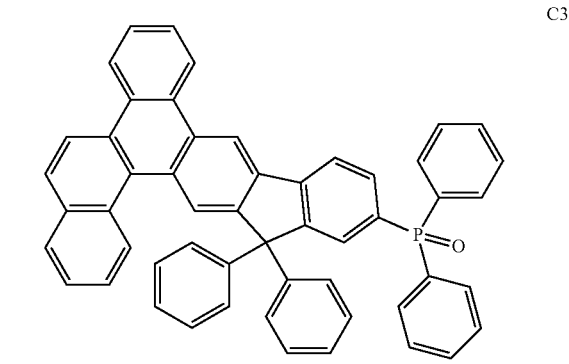
C40
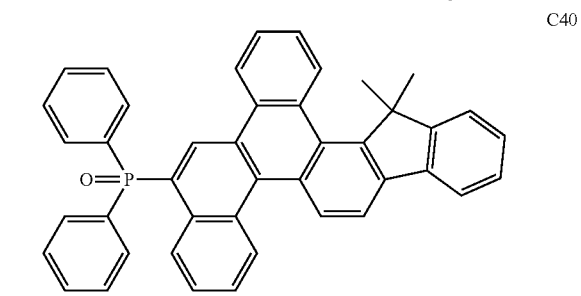
C41
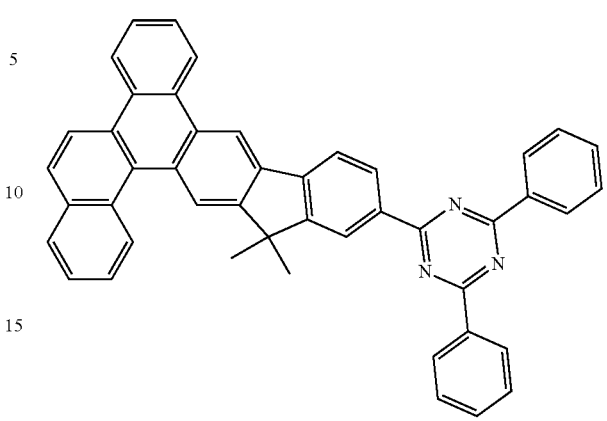
C42
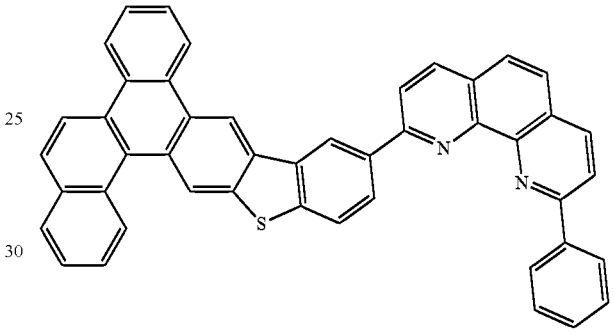
C43
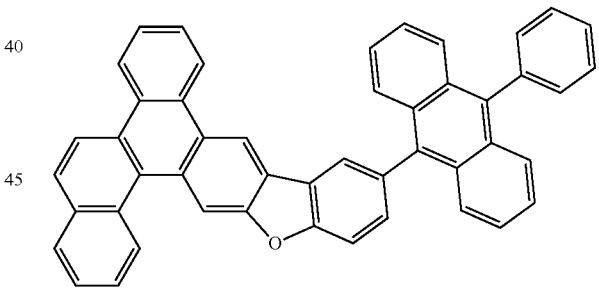
C44
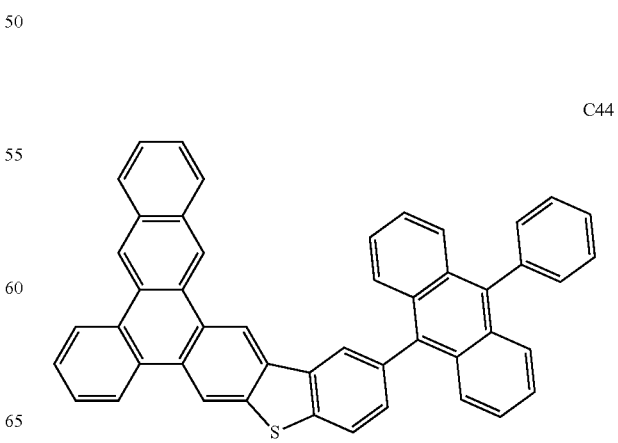

C45
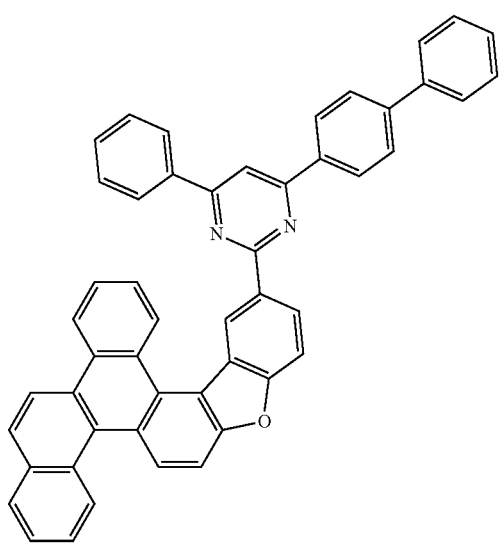
C46
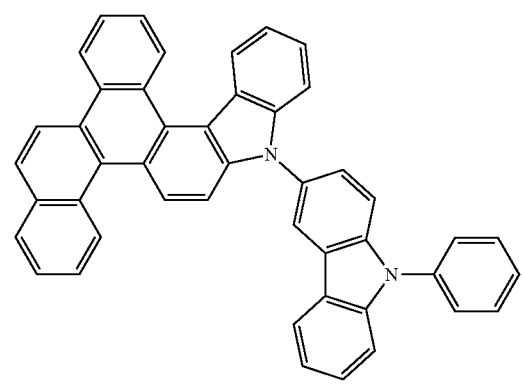
C47
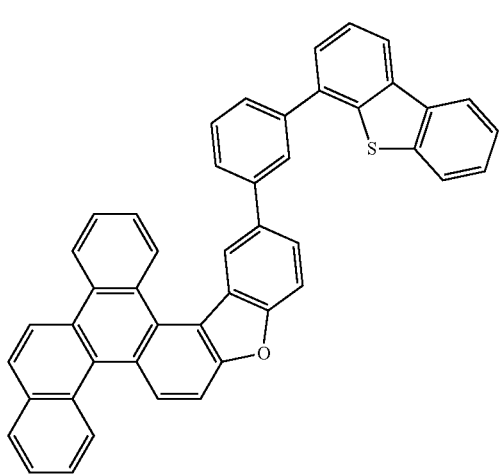
C48
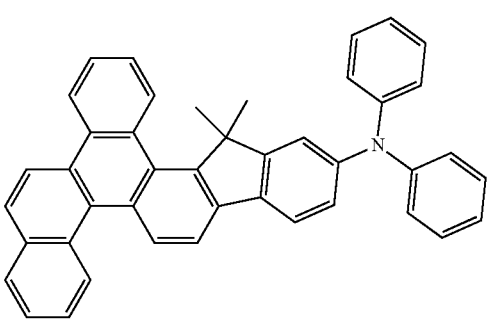
C49
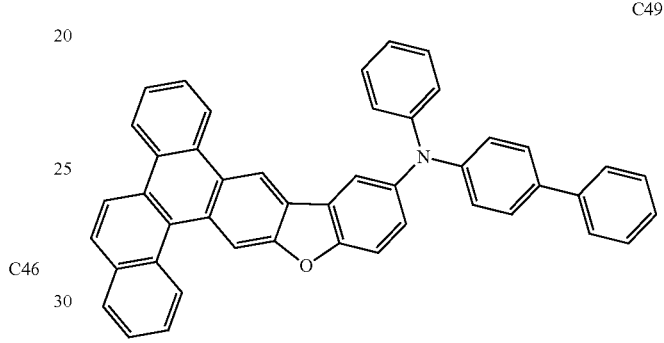
C50
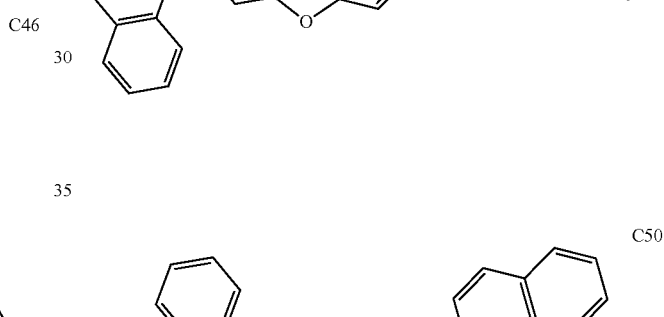
C51
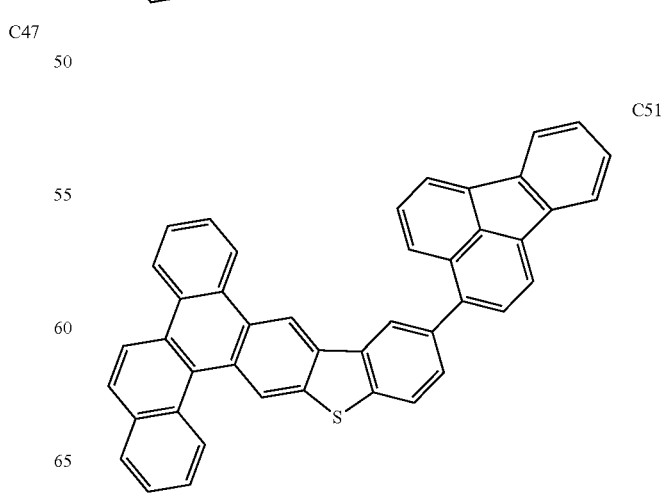

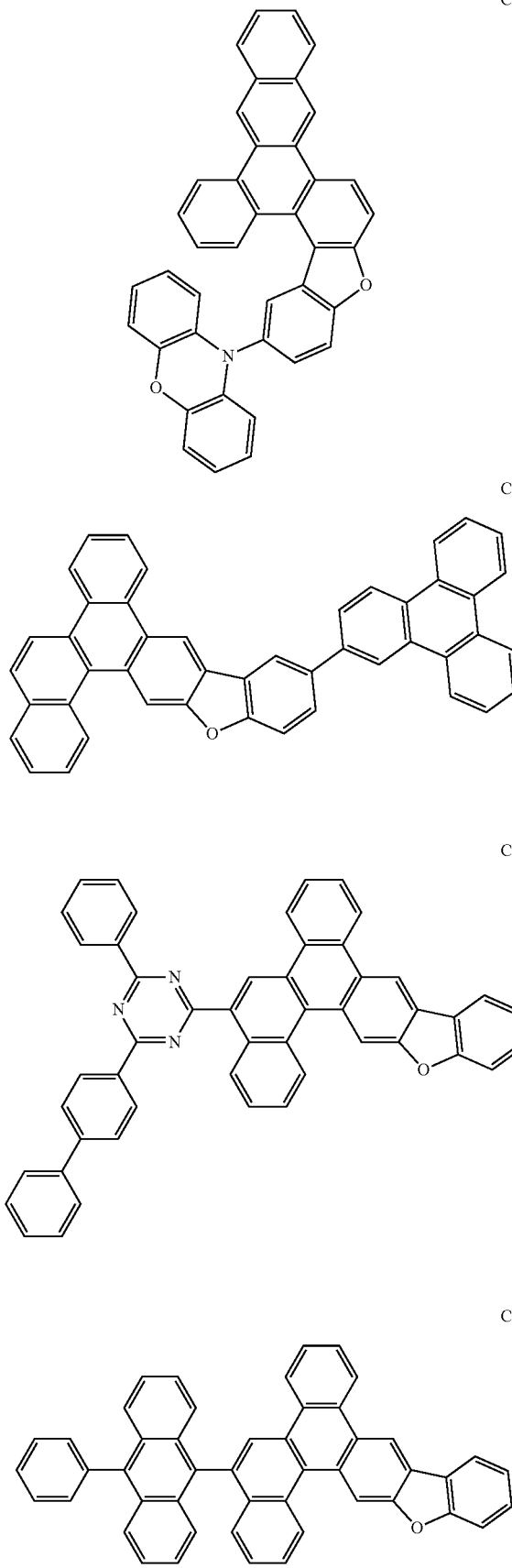
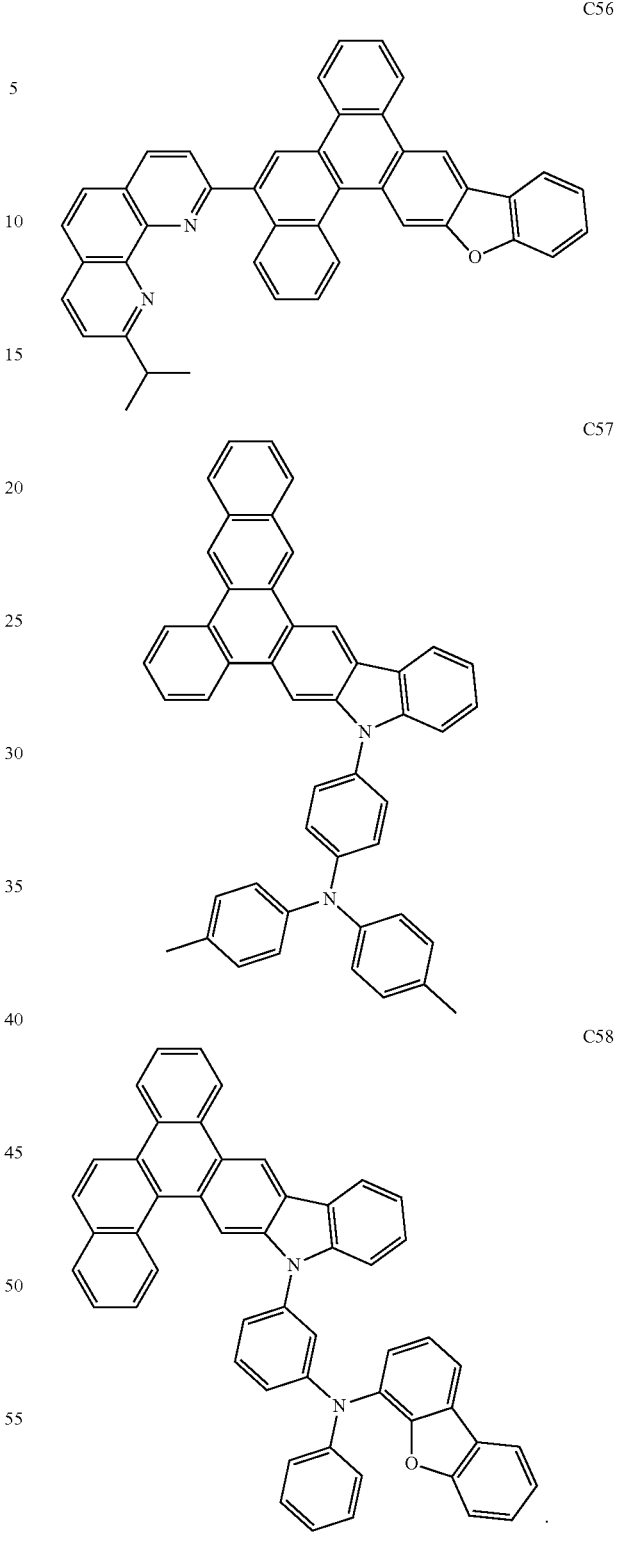
In another embodiment of the present invention, an organic electroluminescence device is disclosed. The organic electroluminescence device comprises a pair of electrodes composed of a cathode and an anode, and a light emitting layer and one or more organic thin film layers between the pair of electrodes. At least one of the light emitting layer and the organic thin film layer comprises the organic compound of formula (1) or formula (2).

In some embodiments, the light emitting layer comprising the organic compound of formula (1) or formula (2) is a host material. The host material may be a phosphorescent host material or a fluorescent host material. In certain embodiments, the light emitting layer comprising the organic compound of formula (1) or formula (2) is used as a fluorescent dopant material.

In some embodiments, the organic thin film layer comprising the organic compound of formula (1) or formula (2) is an electron transporting layer.

In a further embodiment of the present invention, the organic electroluminescence device is a lighting panel. In other embodiment of the present invention, the organic electroluminescence device is a backlight panel.

Detailed preparation of the organic compounds of the present invention will be clarified by exemplary embodiments below, but the present invention is not limited thereto. EXAMPLES 1 to 8 show the preparation of the organic compounds of the present invention, and EXAMPLES 9 to 11 show the fabrication and test reports of the organic EL devices.

Example 1

Synthesis of Compound C41
Synthesis of Intermediate A1

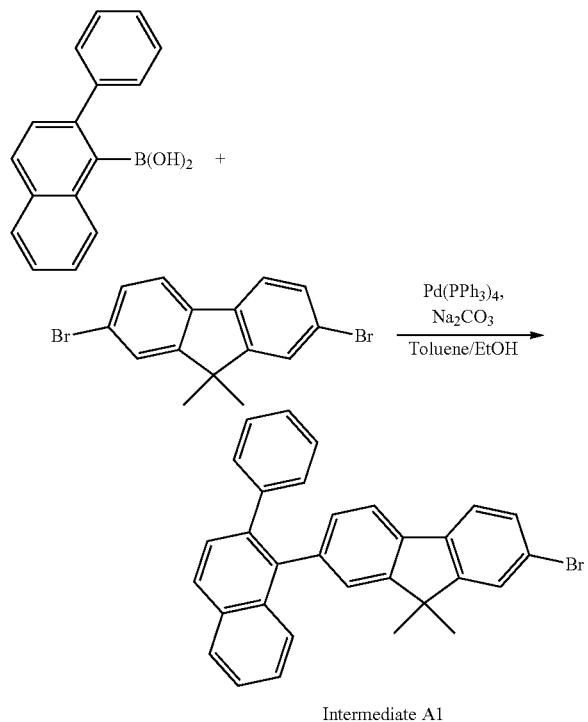

A mixture of 3 g (12.1 mmol) of 2-phenylnaphthalen-1-ylboronic acid, 4.2 g (12.1 mmol) of 2,7-dibromo-9,9-dimethyl-9H-fluorene, 0.28 g (0.24 mmol) of Pd(PPh$_3$)$_4$, 10 ml of 2M Na$_2$CO$_{3(aq)}$, 10 ml of EtOH, and 30 ml of toluene was degassed and placed under nitrogen, and then heated at 100° C. for 6 hrs. After the reaction finished, the mixture was allowed to cool to room temperature. Subsequently, the organic layer was extracted with ethyl acetate and water, and then dried with anhydrous magnesium sulfate. After the solvent was removed, the residue was purified by column chromatography on silica to give Intermediate A1 (3.6 g, 63.1%).

Synthesis of Intermediate A2

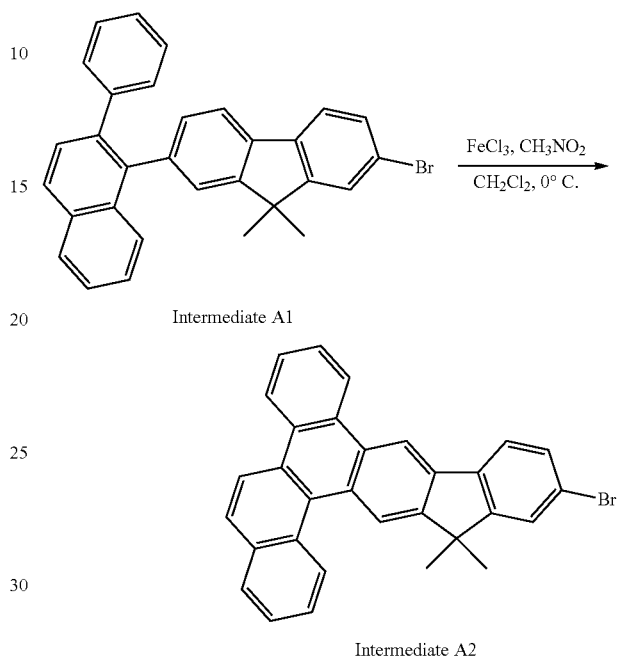

In a 500 ml three-necked flask that had been degassed and filled with nitrogen, 5.0 g (10.5 mmol) of Intermediate A1 was dissolved in anhydrous dichloromethane (300 ml), and then 17 g (105 mmol) of Iron(III) chloride was added thereto. After stirring for one hour, 500 ml of nitromathane was added thereto, and then the organic layer was separated and removed the solvent in vacuum. The residue was purified by column chromatography on silica (hexane-dichloromethane) to afford a white solid (2.0 g, 40%).

Synthesis of Intermediate A3

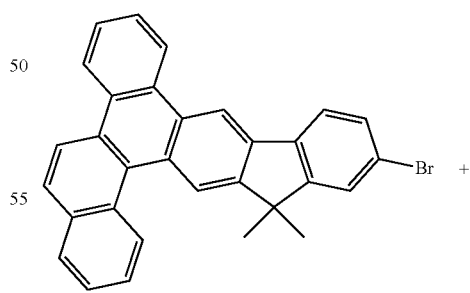

Intermediate A2

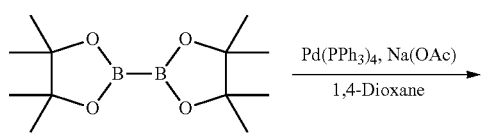

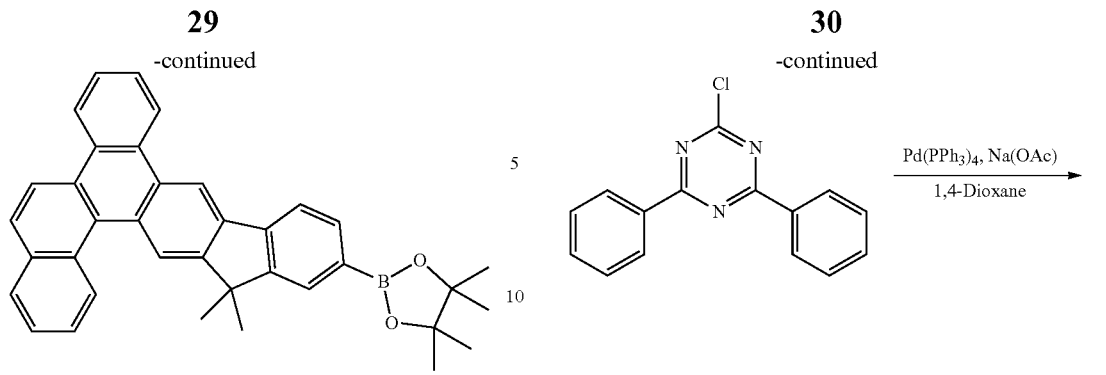

Intermediate A3

A mixture of 2 g (3.8 mmol) of Intermediate A2, 1.6 g (6.3 mmol) of 4,4,4',4',5,5,5',5'-octamethyl-2,2'-bi(1,3,2-dioxaborolane), 0.09 g (0.077 mmol) of Pd(PPh₃)₄, 1.2 g (15.2 mmol) of sodium acetate, and 60 ml of 1,4-dioxane was degassed and placed under nitrogen, and then heated at 100° C. for 6 hrs. After the reaction finished, the mixture was allowed to cool to room temperature.

Subsequently, the organic layer was extracted with ethyl acetate and water, and then dried with anhydrous magnesium sulfate. After the solvent was removed, the residue was purified by column chromatography on silica to give Intermediate A3 (1.7 g, 80%).

Synthesis of Compound C41

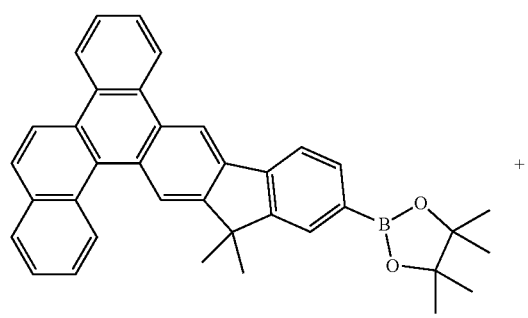

Intermediate A3

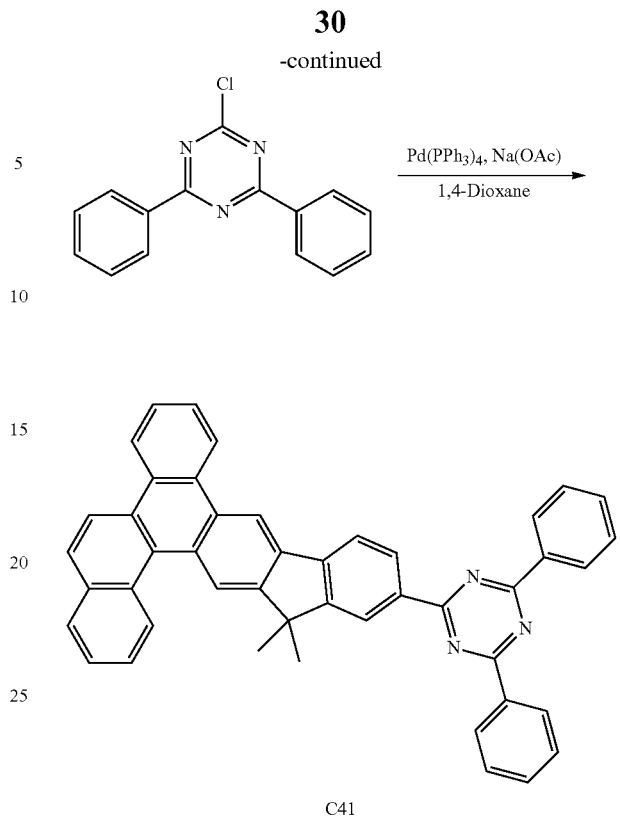

C41

A mixture of 2 g (3.8 mmol) of Intermediate A3, 1.1 g (7.6 mmol) of 2-chloro-4,6-diphenyl-1,3,5-triazine, 0.08 g (0.07 mmol) of Pd(PPh₃)₄, 4 ml of 2M $Na_2CO_{3(aq)}$, 10 ml of EtOH, and 30 ml of toluene was degassed and placed under nitrogen, and then heated at 100° C. for 12 hrs. After the reaction finished, the mixture was allowed to cool to room temperature. Subsequently, the organic layer was extracted with dichloromethane and water, and then dried with anhydrous MgSO₄. After the solvent was removed, the residue was purified by column chromatography on silica to give compound C41 (2.2 g, 53%). MS(m/z, EI⁺): 1117.25.

Example 2

Synthesis of Compound C18
Synthesis of Compound C18

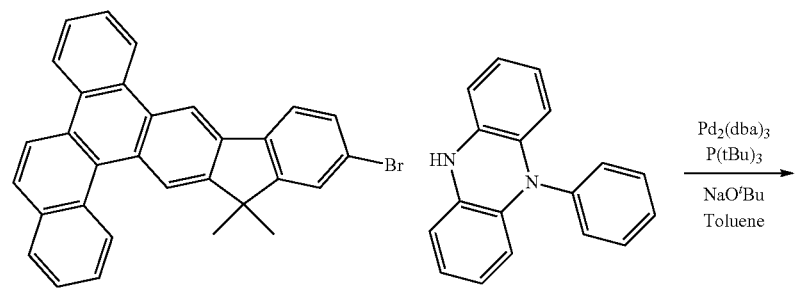

Intermediate A2

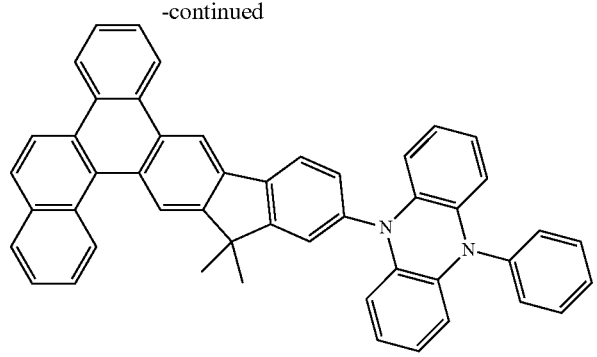

C18

A mixture of 2.0 g (4.2 mmol) of Intermediate A2, 1.2 g (4.6 mmol) of 5-phenyl-5,10-dihydrophenazine, 0.07 g (0.08 mmol) of $Pd_2(dba)_3$, 0.04 g (0.21 mmole) of tri-tert-butylphosphine, 1.2 g (12.6 mmol) of sodium tert-butoxide, and 30 ml of toluene was degassed and placed under nitrogen gas, and then heated at 110° C. for 16 hrs. After the reaction finished, the mixture was allowed to cool to room temperature. Subsequently, the organic layer was extracted with dichloromethane and water, and then dried with anhydrous $MgSO_4$. After the solvent was removed, the residue was purified by column chromatography on silica to give compound C18 (2.6 g, 72%). MS(m/z, EI$^+$): 866.25.

Example 3

Synthesis of Compound C37
Synthesis of Intermediate A4

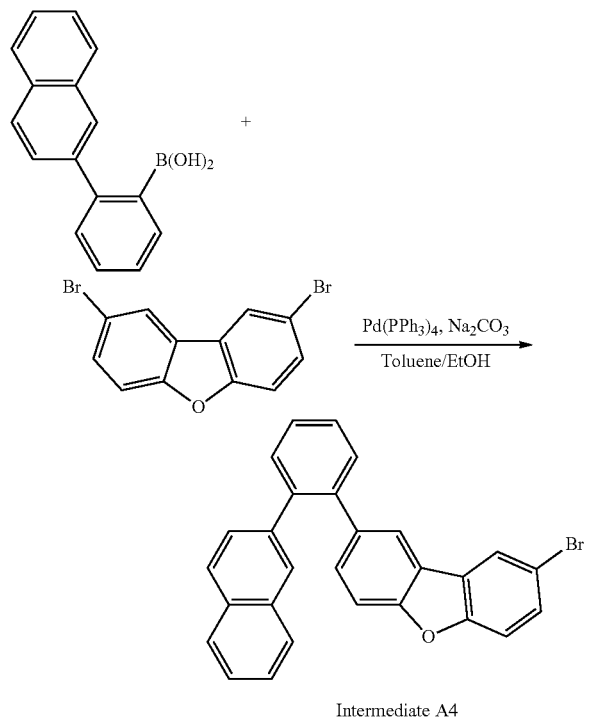

Intermediate A4

The same synthesis procedure as in Synthesis of Intermediate A1 was used, except that 3.0 g of 2-(naphthalen-2-yl)phenylboronic acid was used instead of 2-phenylnaphthalen-1-ylboronic acid and 3.9 g of 2,8-dibromodibenzo[b,d]furan was used instead of 2,7-dibromo-9,9-dimethyl-9H-fluorene to obtain the desired Intermediate A4 (3.3 g, yield=61%).

Synthesis of Intermediate A5

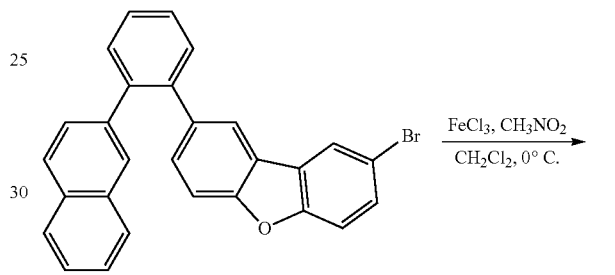

Intermediate A4

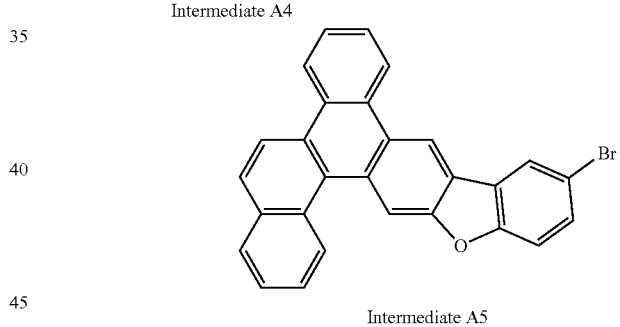

Intermediate A5

The same synthesis procedure as in Synthesis of Intermediate A2 was used, except that 3.0 g of Intermediate A4 was used instead of Intermediate A1 to obtain the desired Intermediate A5 (1.7 g, yield=58.2%).

Synthesis of Intermediate A6

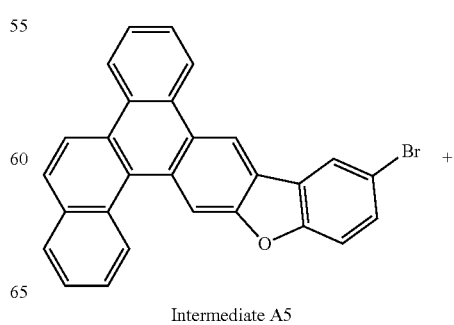

Intermediate A5

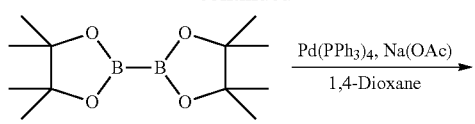

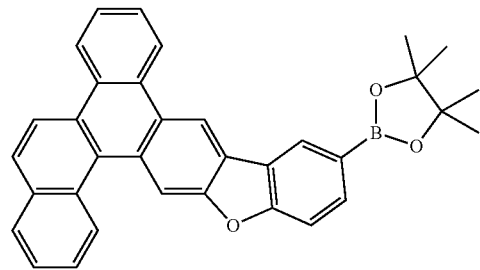

Intermediate A6

The same synthesis procedure as in Synthesis of Intermediate A3 was used, except that 3 g of Intermediate A5 was used instead of Intermediate A2 to obtain the desired Intermediate A6 (2.4 g, yield=74%).

Synthesis of Compound C37

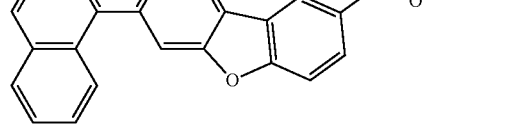

Intermediate A6

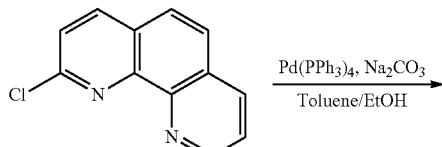

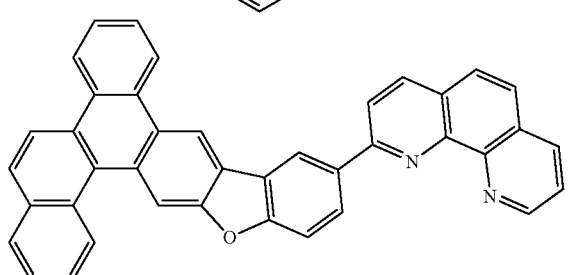

C37

The same synthesis procedure as in Synthesis of Compound C41 was used, except that 3 g of Intermediate A6 was used instead of Intermediate A3 and 1.4 g of 2-chloro-1,10-phenanthroline was used instead of 2-chloro-4,6-diphenyl-1,3,5-triazine to obtain the desired Compound C37 (4.7 g, yield=79.3%). MS(m/z, EI+): 990.16.

Example 4

Synthesis of Compound C43
Synthesis of Compound C43

Intermediate A6

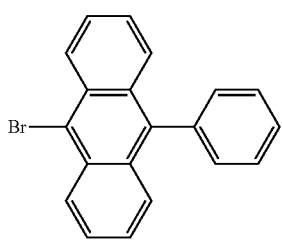

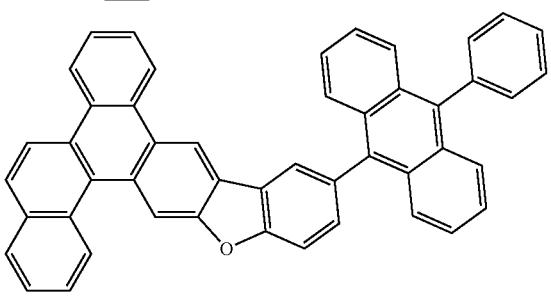

C43

The same synthesis procedure as in Synthesis of Compound C41 was used, except that 3 g of Intermediate A6 was used instead of A3 and 2.0 g of 9-bromo-10-phenylanthracene was used instead of 2-chloro-4,6-diphenyl-1,3,5-triazine to obtain the desired Compound C43 (5.2 g, yield=76.3%).

Example 5

Synthesis of Compound C54
Synthesis of Intermediate A7

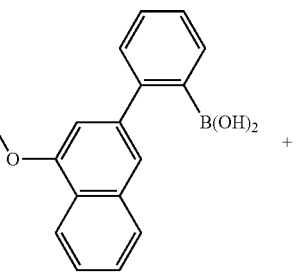

-continued

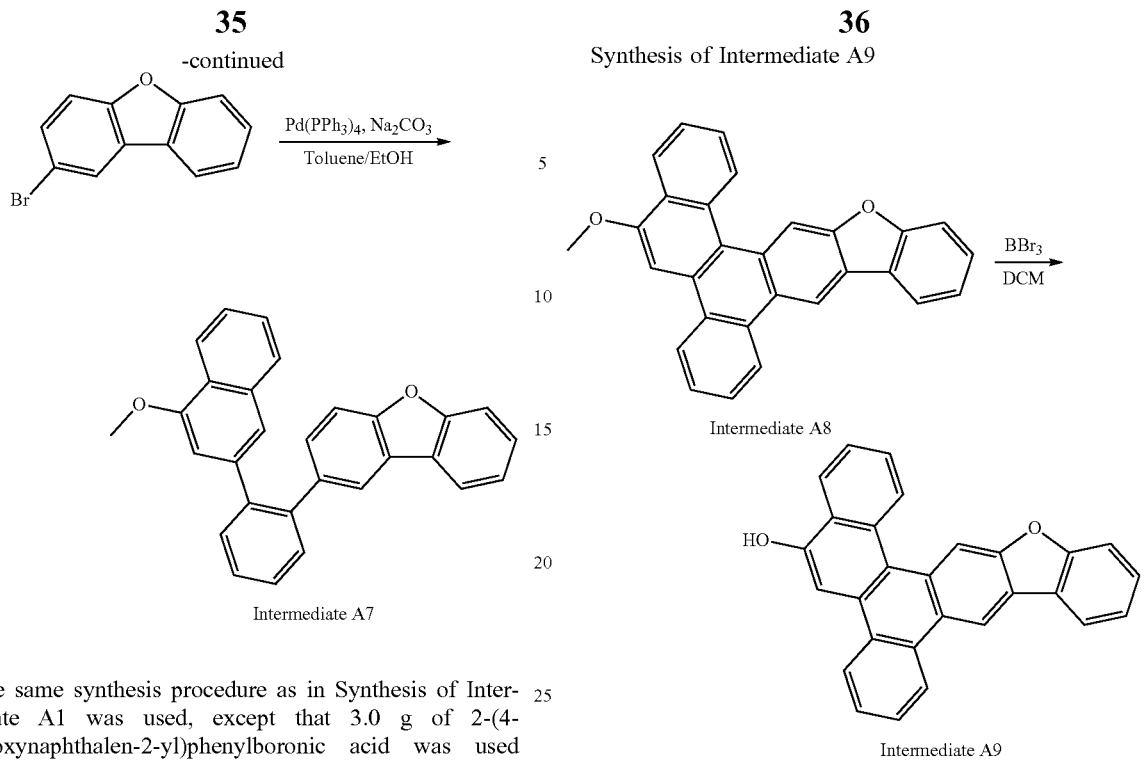

The same synthesis procedure as in Synthesis of Intermediate A1 was used, except that 3.0 g of 2-(4-methoxynaphthalen-2-yl)phenylboronic acid was used instead of 2-phenylnaphthalen-1-ylboronic acid and 2.6 g of 2-bromodibenzo[b,d]furan was used instead of 2,7-dibromo-9,9-dimethyl-9H-fluorene to obtain the desired Intermediate A7 (3.8 g, yield=88.5%).

Synthesis of Intermediate A8

The same synthesis procedure as in Synthesis of Intermediate A2 was used, except that 3.0 g of Intermediate A7 was used instead of Intermediate A1 to obtain the desired Intermediate A8 (1.7 g, yield=56.2%).

Synthesis of Intermediate A9

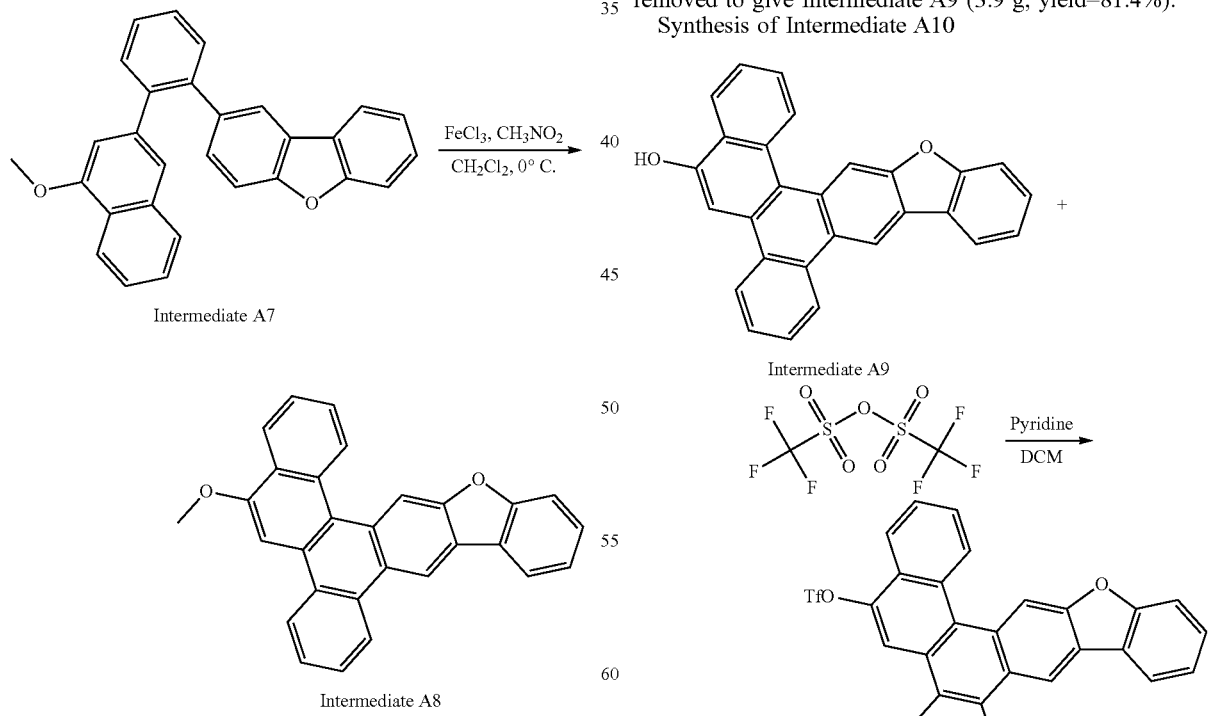

A mixture of 5 g (12.5 mmol) of Intermediate A8 and 60 ml of dichloromethane was placed into the reactor under nitrogen. Boron tribromide (1 eq.) was added thereto and then stirred for 2 hrs until the reaction finished. The reaction mixture was extracted with dichloromethane and water, and then dried with anhydrous $MgSO_4$. The solvent was removed to give Intermediate A9 (3.9 g, yield=81.4%).

Synthesis of Intermediate A10

A mixture of 2.6 g (6.76 mmol) of Intermediate A9 and 60 ml of dichloromethane was placed into the reactor under nitrogen. Pyridine (1.5 eq.) and trifluoromethanesulfonic anhydride (1.7 eq) was added thereto and then stirred for 12 hrs until the reaction finished. The reaction mixture was extracted with dichloromethane and water, and then dried with anhydrous MgSO₄. The solvent was removed to give Intermediate A10 (3.1 g, yield=90%).

Synthesis of Intermediate A11

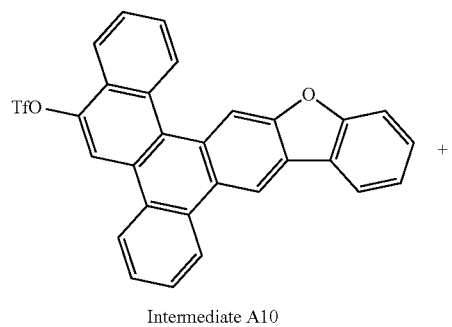

Intermediate A10

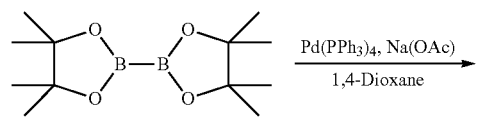

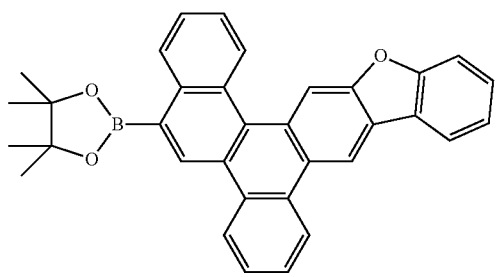

Intermediate A11

The same synthesis procedure as in Synthesis of Intermediate A3 was used, except that 2.9 g of Intermediate A10 was used instead of Intermediate A2 to obtain the desired Intermediate A11 (2.0 g, yield=73.6%).

Synthesis of Compound C54

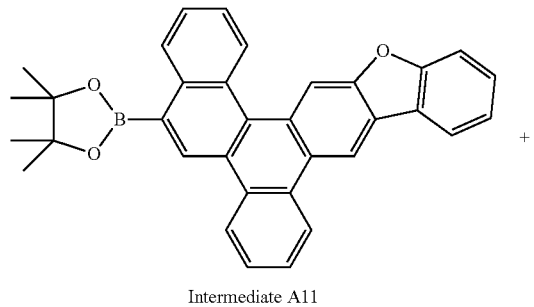

Intermediate A11

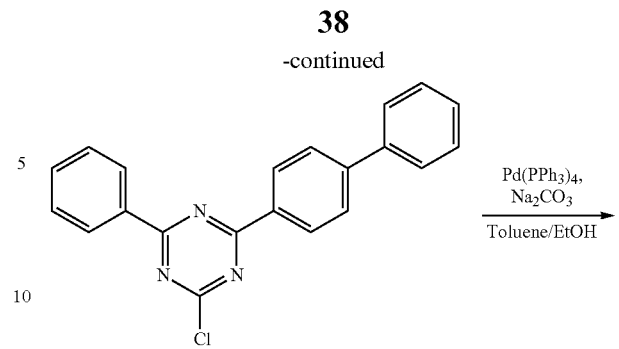

C54

The same synthesis procedure as in Synthesis of Compound C41 was used, except that 3 g of Intermediate A11 was used instead of A3 and 2.1 g of 2-(biphenyl-4-yl)-4-chloro-6-phenyl-1,3,5-triazine was used instead of 2-chloro-4,6-diphenyl-1,3,5-triazine to obtain the desired Compound C54 (5.6 g, yield=69.8%).

Example 6

Synthesis of Compound C25

Synthesis of Intermediate A12

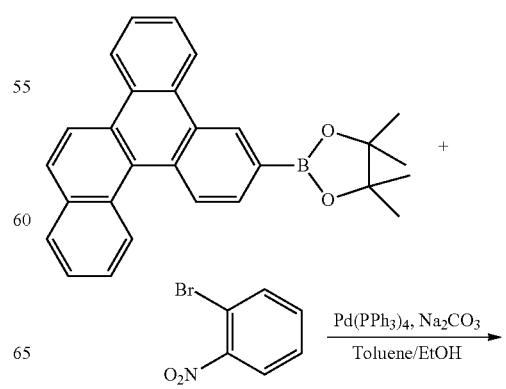

Synthesis of Compound C25

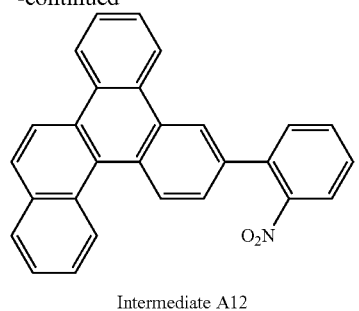

Intermediate A12

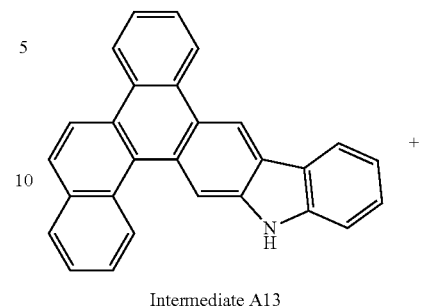

Intermediate A13

The same synthesis procedure as in Synthesis of Compound C41 was used, except that 5 g of 2-(benzo[g]chrysen-3-yl)-4,4,5,5-tetramethyl-1,3,2-dioxaborolane was used instead of Intermediate A3 and 2.5 g of 1-bromo-2-nitrobenzene was used instead of 2-chloro-4,6-diphenyl-1,3,5-triazine to obtain the desired Intermediate A12 (3.6 g, yield=74.1%).

Synthesis of Intermediate A13

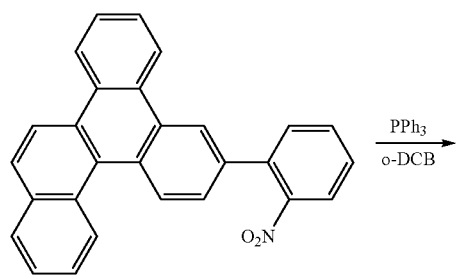

Intermediate A12

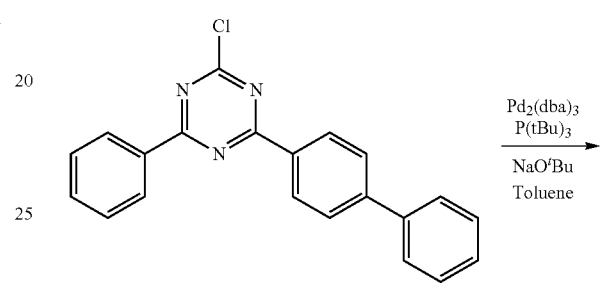

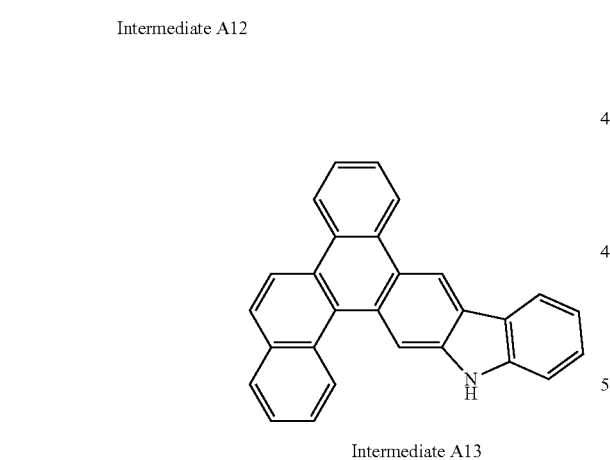

Intermediate A13

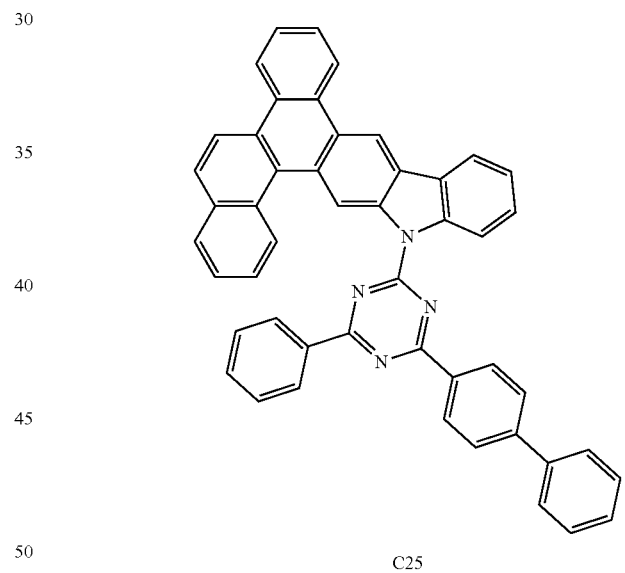

C25

A mixture of 2 g (5.0 mmol) of Intermediate A12, 13.1 g (50.0 mmol) of Triphenylphosphine, and 30 ml of o-DCB was placed under nitrogen gas, and then heated at 180° C. for 8 hrs. After the reaction finished, the mixture was allowed to cool to room temperature. The mixture was poured into water, and then filtered to give Intermediate A13 (0.9 g, 50%).

A mixture of 3.0 g (8.1 mmol) of Intermediate A13, 3.1 g (4.6 mmol) of 2-(biphenyl-4-yl)-4-chloro-6-phenyl-1,3,5-triazine, 0.15 g (0.16 mmol) of $Pd_2(dba)_3$, 0.03 g (0.16 mmole) of tri-tert-butylphosphine, 2.3 g (24.3 mmol) of sodium tert-butoxide, and 60 ml of toluene was degassed and placed under nitrogen gas, and then heated at 110° C. for 16 hrs. After the reaction finished, the mixture was allowed to cool to room temperature. Subsequently, the organic layer was extracted with dichloromethane and water, and then dried with anhydrous $MgSO_4$. After the solvent was removed, the residue was purified by column chromatography on silica to give compound C25 (5.9 g, 74.1%). MS(m/z, EI$^+$): 974.21.

Example 7

Synthesis of Compound C49
Synthesis of Compound C49

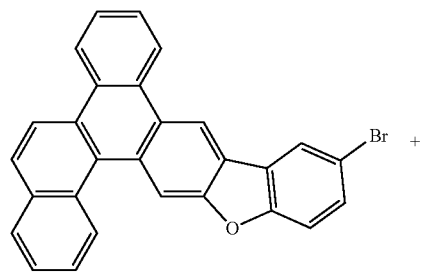

Intermediate A5

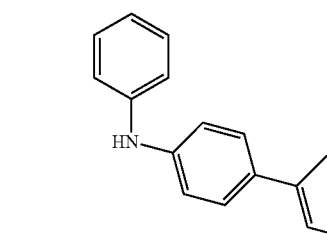

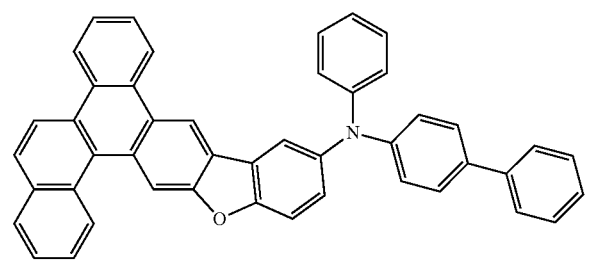

C49

A mixture of 3.0 g (6.6 mmol) of Intermediate A5, 1.6 g (7.2 mmol) of N-phenylbiphenyl-4-amine, 0.12 g (0.13 mmol) of Pd$_2$(dba)$_3$, 0.03 g (0.16 mmole) of tri-tert-butylphosphine, 2.0 g (19.8 mmol) of sodium tert-butoxide, and 60 ml of toluene was degassed and placed under nitrogen gas, and then heated at 110° C. for 16 hrs. After the reaction finished, the mixture was allowed to cool to room temperature. Subsequently, the organic layer was extracted with dichloromethane and water, and then dried with anhydrous MgSO$_4$. After the solvent was removed, the residue was purified by column chromatography on silica to give compound C49 (6.6 g, 82.3%). MS(m/z, EI$^+$): 1199.23.

Example 8

Synthesis of Compound C58
Synthesis of Compound C58

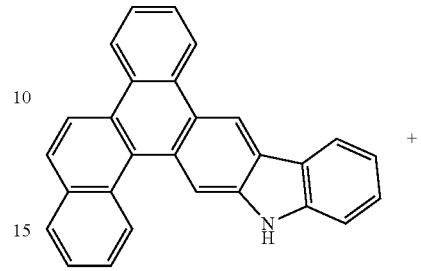

Intermediate A13

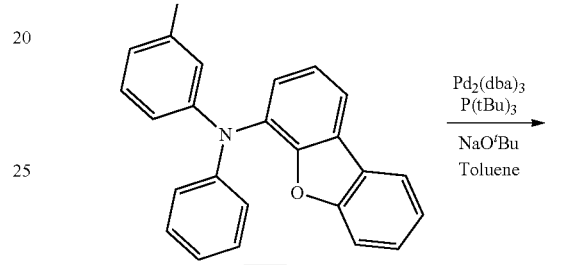

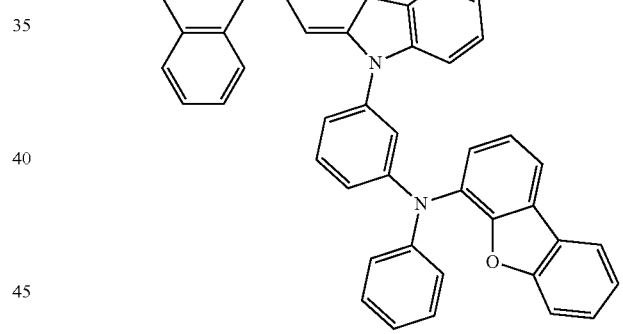

C58

The same synthesis procedure as in Synthesis of Compound C25 was used, except that 3 g of N-(3-bromophenyl)-N-phenyldibenzo[b,d]furan-4-amine was used instead of 2-(biphenyl-4-yl)-4-chloro-6-phenyl-1,3,5-triazine to obtain the desired Compound C58 (7.4 g, yield=74.1%).

General Method of Producing Organic EL Device

ITO-coated glasses with 12 ohm/square in resistance and 120 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrates are under clean room (class 100).

The organic layers are applied onto the ITO substrate in order by vapor deposition in a high-vacuum unit (10$^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is successfully achieved by co-vaporization from two or more sources, which means the organic compounds of the present invention are thermally stable.

Dipyrazino[2,3-f:2,3-]quinoxaline-2,3,6,7,10,11-hexacarbonitrile (HAT-CN) is used to form the hole injection layer, and N,N-bis(naphthalene-1-yl)-N,N-bis(phenyl)-benzidine (NPB) is used to form the hole transporting layer of the organic EL device. 2,9-bis(naphthalene-2-yl)-4,7-diphenyl-1,10-phenanthroline (NPhen) is used as the electron transporting material in organic EL device for its high thermal stability and long life-time than BPhen or BCP. For fluorescence emitting device, 1,1'-(9,9-dimethyl-9H-fluorene-2,7-diyl)dipyrene (DFDP) is used as the host material, and (E)-6-(4-(diphenylamino) styryl)-N,N-diphenylnaphthalen-2-amine (D1) is used as the fluorescent dopant. For phosphorescence emitting device, bis(2-methyl-8-quinolinolate)-4-(phenylphenolato)aluminium (BAlq) is used as the host material of emitting layer, and tris(1-phenylisoquinoline)-Iridium(III) (Ir(piq)$_3$) or tris(2-phenylquinoline)iridium(III) (Ir(2-phq)$_3$) is used as the dopant material. Compounds C9, C10, C11, C12, C13, C34, C43, and C44 are used as the fluorescent host materials to compare with DFDP. Compounds C5, C6, C7, C16, C19 and C49 are used as the fluorescent dopant materials to compare with D1. Compounds C15, C22, C23, C42 and C45 are used as the electron transporting materials to compare with NPhen. Compounds C1, C2, C3, C4, C27, C39, C40 and C58 are used as the phosphorescent host materials to compare with BAlq. The chemical structures of conventional OLED materials and the exemplary organic compounds of the present invention for producing control and exemplary organic EL devices in this invention are shown as follows:

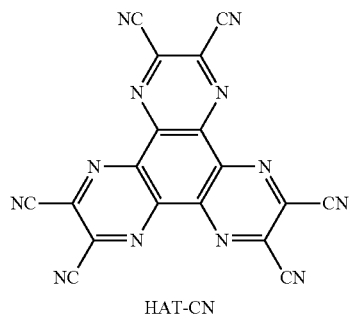

HAT-CN

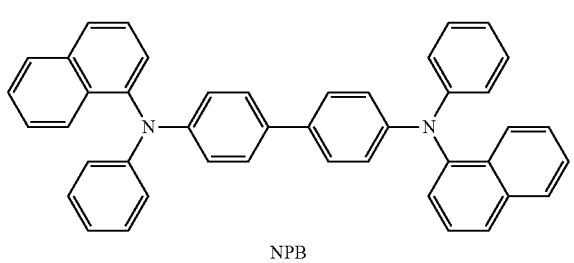

NPB

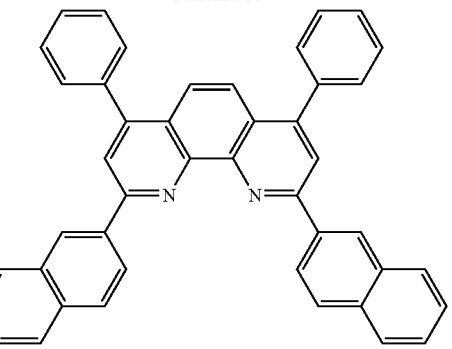

NPhen

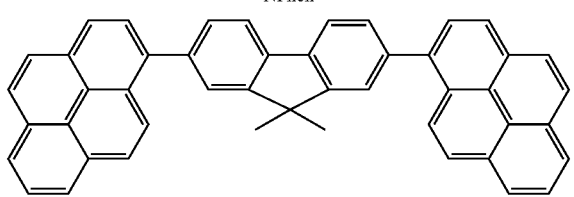

DFDP

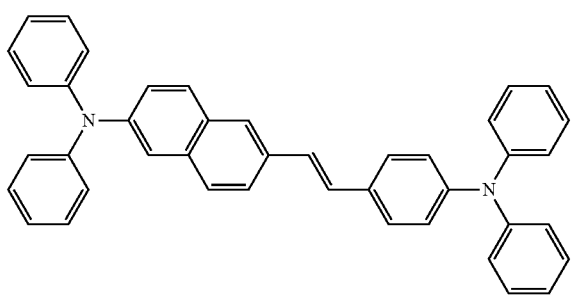

D1

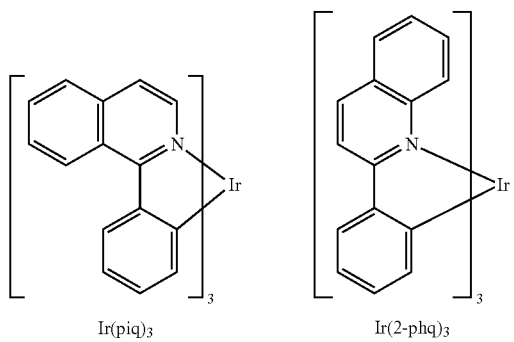

BAlq

Ir(piq)$_3$          Ir(2-phq)$_3$

C1
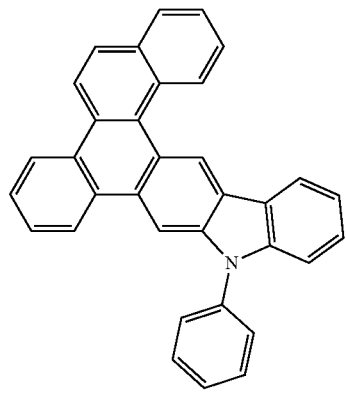
C2
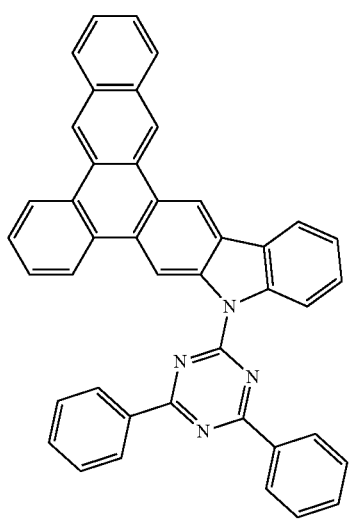
C4
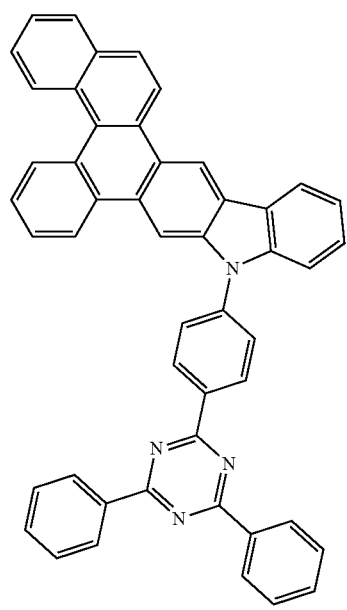
C5
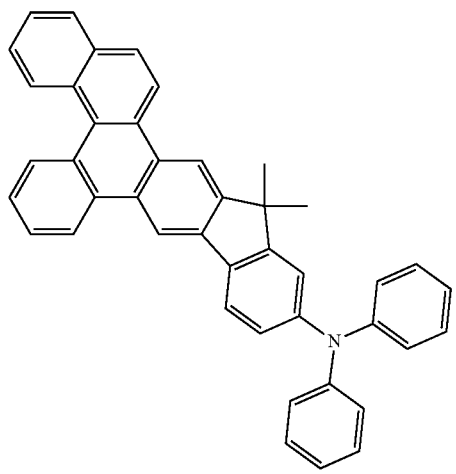
C6
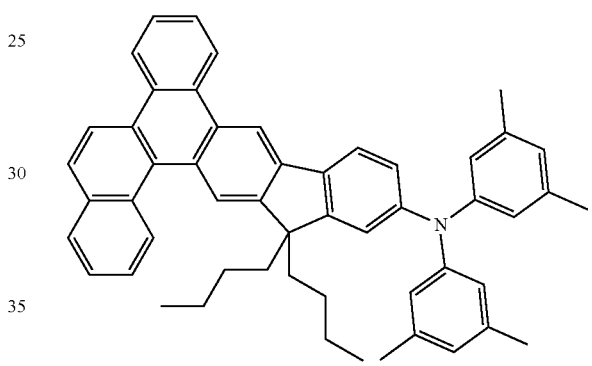
C7
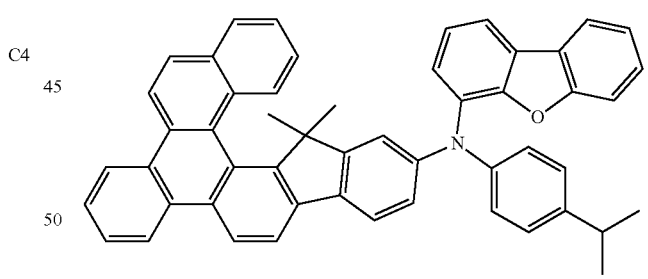
C9
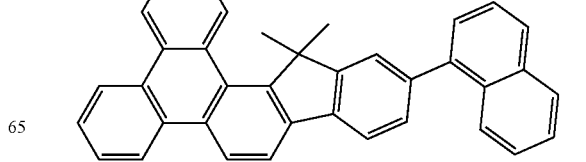

C10
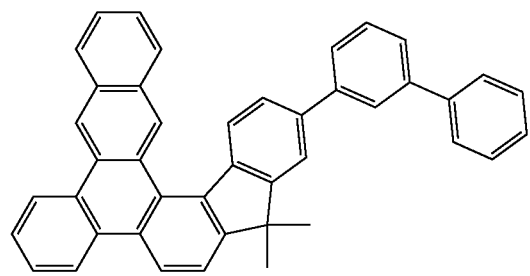
C11
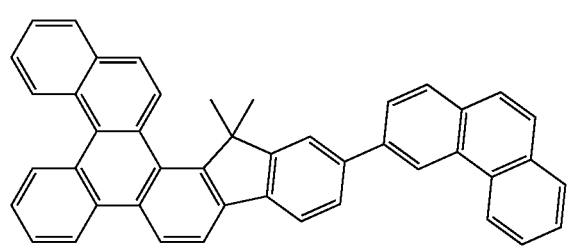
C12
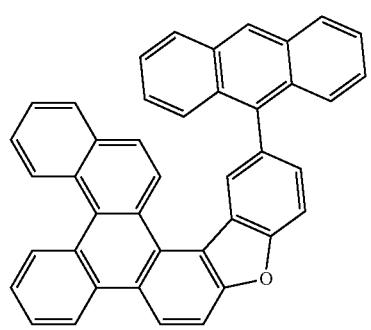
C13
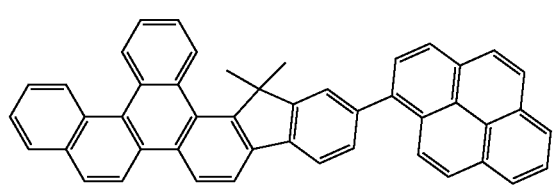
C15
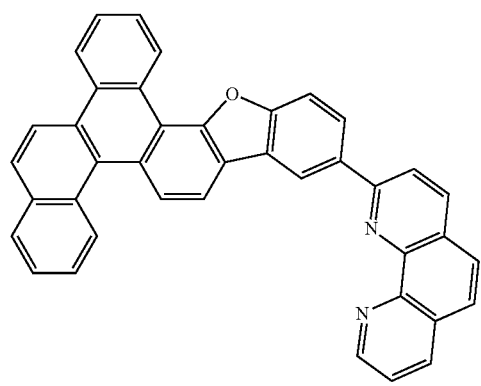
C16
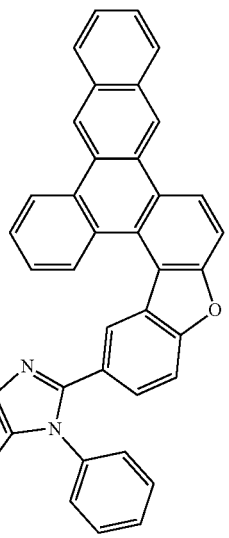
C19
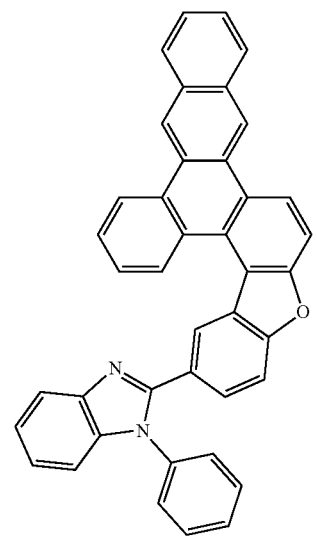
C22
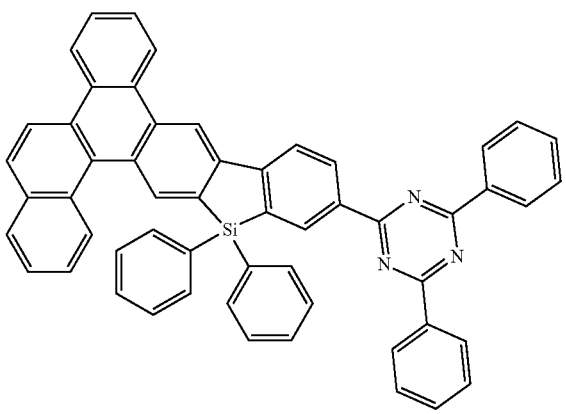

-continued
C23
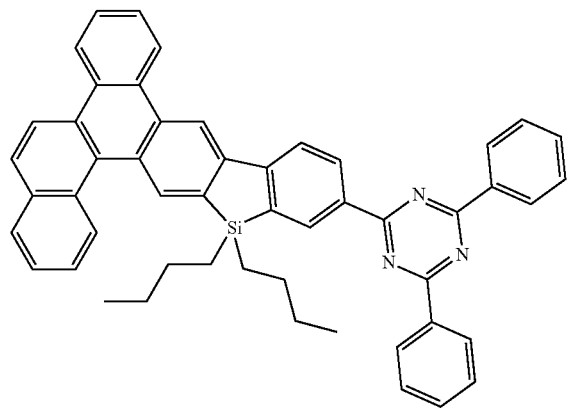
C27
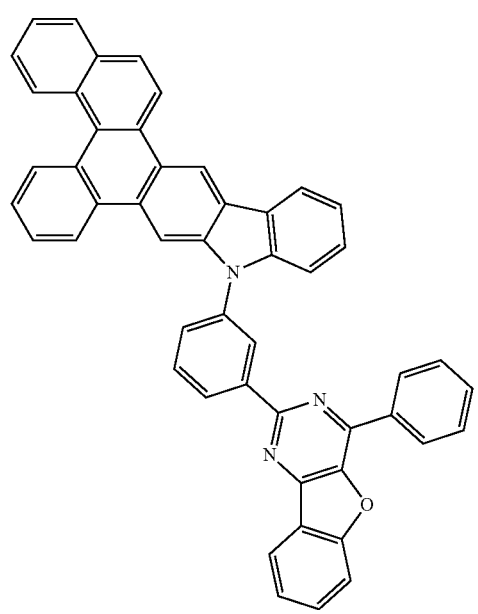
C34
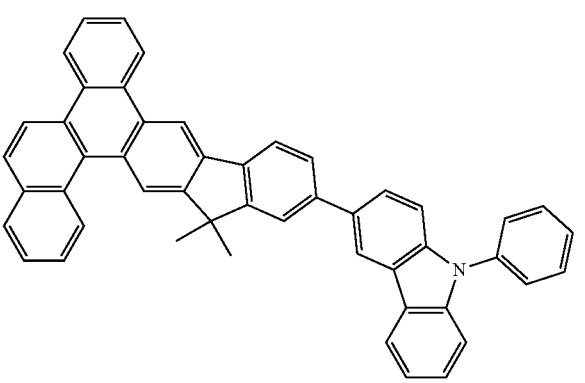
-continued
C39
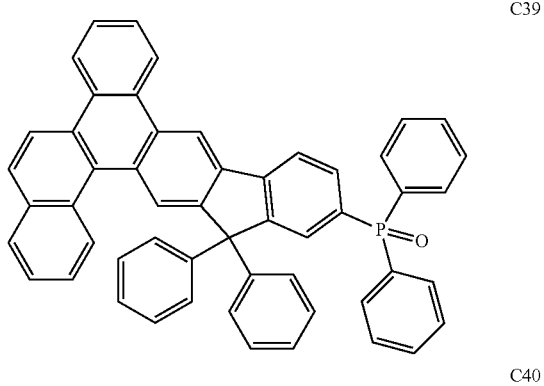
C40
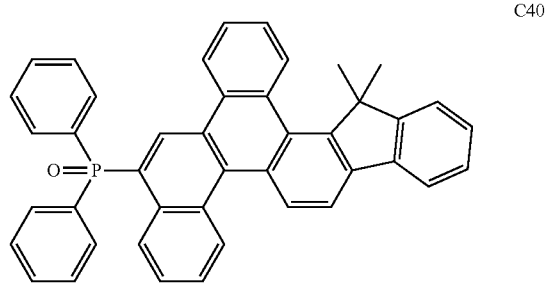
C42
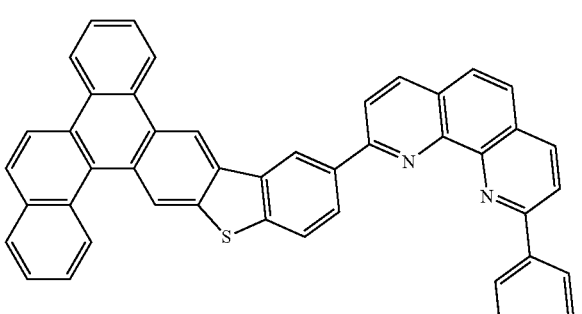
C43
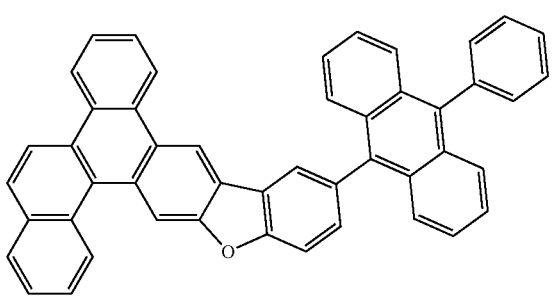
C44
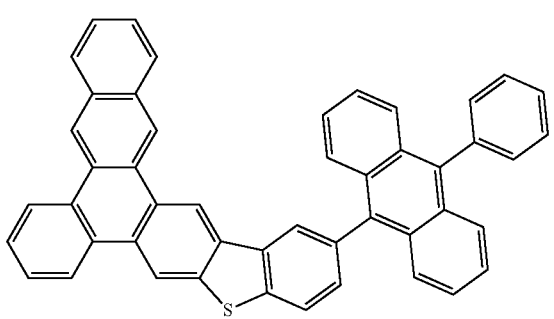

C45

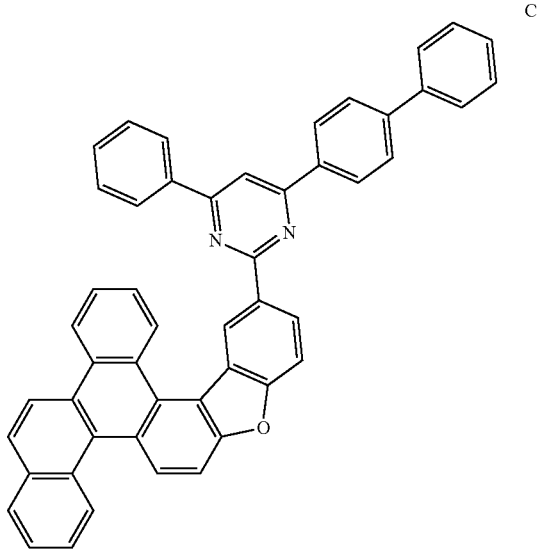

C58

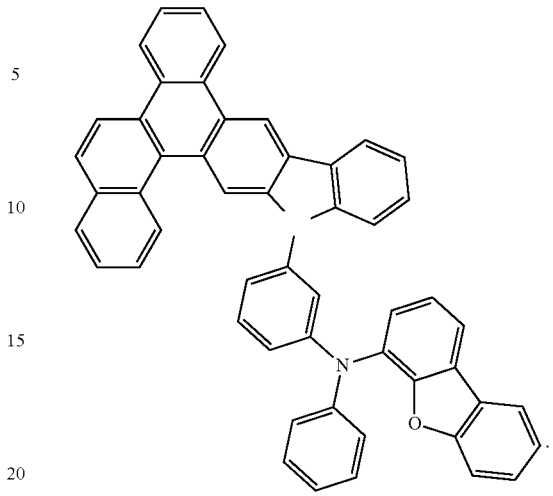

C3

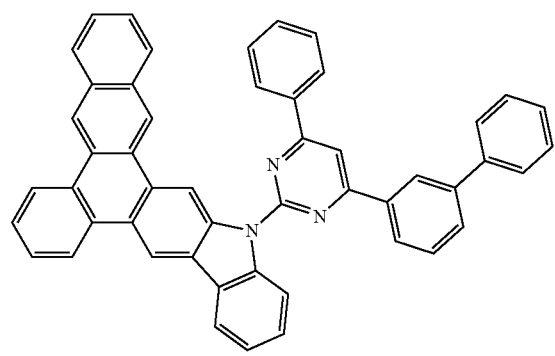

C49

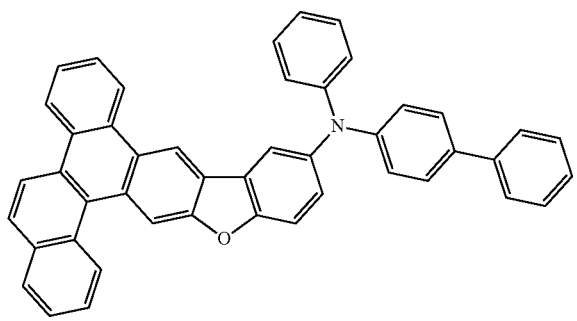

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, MgO, or $Li_2O$.

On the other hand, after the organic EL device fabrication, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

Example 9

Using a procedure analogous to the above-mentioned general method, organic EL devices emitting blue fluorescence and having the following device structure as shown in the FIGURE were produced: ITO/HAT-CN(20 nm)/NPB(50 nm)/fluorescent blue host (DFDP or C9, C10, C11, C12, C13, C34, C43, or C44)+5% dopant(D1 or C5, C6, C7, C16, C19 or C49) (30 nm)/NPhen (30 nm)/LiF (0.5 nm)/Al(160 nm). In the device illustrated in the FIGURE, the hole injection layer 20 is deposited onto the transparent electrode 10, the hole transport layer 30 is deposited onto the hole injection layer 20, the emitting layer 40 is deposited onto the hole transport layer 30, the electron transport layer 50 is deposited onto the emitting layer 40, the electron injection layer 60 is deposited onto the electron transport layer 50, and the metal electrode 70 is deposited onto the electron injection layer 60. The I-V-B and half-life time test reports of these fluorescent blue-emitting organic EL devices are summarized in Table 1 below, and the half-life time is defined as the time the initial luminance of 3000 cd/m² has dropped to half.

TABLE 1

| Fluorescent blue host + 5% dopant | Voltage (V) | Luminance (cd/m²) | Efficiency (cd/A) | CIE (y) | Half-life time (hr) |
|---|---|---|---|---|---|
| DFDP + D1 | 6 | 965 | 5.02 | 0.17 | 300 |
| DFDP + C5 | 6 | 1124 | 5.83 | 0.15 | 410 |
| DFDP + C6 | 6 | 1333 | 6.73 | 0.15 | 436 |
| DFDP + C7 | 6 | 1276 | 6.63 | 0.15 | 442 |
| DFDP + C16 | 6 | 1362 | 6.31 | 0.15 | 450 |
| DFDP + C19 | 6 | 1441 | 6.83 | 0.15 | 421 |
| DFDP + C49 | 6 | 1584 | 8.21 | 0.14 | 492 |
| C9 + D1 | 6 | 1165 | 5.63 | 0.15 | 400 |
| C10 + D1 | 6 | 1122 | 5.52 | 0.15 | 314 |
| C11 + D1 | 6 | 998 | 5.13 | 0.15 | 323 |
| C12 + D1 | 6 | 1255 | 6.36 | 0.15 | 389 |
| C13 + D1 | 6 | 1050 | 5.24 | 0.15 | 332 |
| C34 + D1 | 6 | 1181 | 5.58 | 0.15 | 392 |
| C43 + D1 | 6 | 1436 | 6.66 | 0.15 | 434 |
| C44 + D1 | 6 | 1231 | 6.45 | 0.15 | 411 |

From the above test report summary of the organic EL devices, it is obvious that the organic compound of formula (1) or formula (2) used as the fluorescent blue host or dopant material exhibits better performance than the prior art materials. In particular, the organic EL devices of the present invention employing the organic compound of formula (1) or formula (2) as the dopant material or host material to collocate with the host material DFDP or the dopant material D1 have improved luminance, current efficiency, and half-life time under the same voltage.

Example 10

Using a procedure analogous to the above-mentioned general method, organic EL devices having the following device structure were produced: ITO/HAT-CN(20 nm)/NPB (50 nm)/DFDP+5% D1 (30 nm)/NPhen or C15, C22, C23, C42 or C45 (30 nm)/LiF(0.5 nm)/Al(160 nm). The I-V-B and half-life time test reports of these blue fluorescence-emitting organic EL devices are summarized in Table 2 below, and the half-life time is defined as the time the initial luminance of 3000 cd/m² has dropped to half.

TABLE 2

| ETM | Voltage (V) | Efficiency (cd/A) | CIE (y) | Half-life time (hr) |
|---|---|---|---|---|
| NPhen | 6.2 | 5.12 | 0.17 | 310 |
| C15 | 4.5 | 8.61 | 0.17 | 483 |
| C22 | 4.8 | 7.82 | 0.17 | 423 |
| C23 | 4.7 | 7.43 | 0.17 | 410 |
| C42 | 4.7 | 8.53 | 0.17 | 490 |
| C45 | 4.6 | 8.32 | 0.17 | 488 |

From the summary of the test report the above organic EL devices, it can be seen that the organic compound of formula (1) or formula (2) used as the electron transporting material exhibits better performance than the prior art material NPhen. In particular, the organic EL device of the present invention using the organic compound of formula (1) or formula (2) as the electron transporting material to collocate with the host material DFDP and the dopant material D1 has lower power consumption, higher current efficiency, and longer half-life time.

Example 11

Using a procedure analogous to the above-mentioned general method, organic EL devices emitting phosphorescence and having the following device structure were produced: ITO/HAT-CN(20 nm)/NPB(50 nm)/phosphorescent host (C1, C2, C3, C4, C27, C39, C40 or C58)+10% dopant (30 nm)/NPhen (30 nm)/LiF(0.5 nm)/Al(160 nm). The I-V-B and half-life time test reports of these phosphorescence emitting organic EL devices are summarized in Table 3 below, and the half-life time is defined as the time the initial luminance of 3000 cd/m² has dropped to half.

TABLE 3

| Phosphorescent host + 10% dopant | Voltage (V) | Luminance (cd/m²) | Efficiency (cd/A) | Device color | Half-life time (hr) |
|---|---|---|---|---|---|
| BAlq + Ir(piq)₃ | 6 | 671 | 8.14 | red | 450 |
| C1 + Ir(piq)₃ | 6 | 900 | 10.55 | red | 550 |
| C2 + Ir(piq)₃ | 6 | 1135 | 13.40 | red | 820 |
| C3 + Ir(piq)₃ | 6 | 1185 | 12.53 | red | 717 |
| C4 + Ir(piq)₃ | 6 | 1341 | 15.05 | red | 891 |
| C27 + Ir(piq)₃ | 6 | 1231 | 14.23 | red | 834 |
| C39 + Ir(piq)₃ | 6 | 910 | 11.28 | red | 651 |
| C40 + Ir(piq)₃ | 6 | 1080 | 13.28 | red | 778 |
| C58 + Ir(piq)₃ | 6 | 1113 | 11.83 | red | 751 |
| BAlq + Ir(2-phq)₃ | 6 | 511 | 14.12 | yellow | 472 |
| C1 + Ir(2-phq)₃ | 6 | 1010 | 28.31 | yellow | 852 |
| C2 + Ir(2-phq)₃ | 6 | 1220 | 35.36 | yellow | 998 |
| C3 + Ir(2-phq)₃ | 6 | 1059 | 29.46 | yellow | 775 |
| C4 + Ir(2-phq)₃ | 6 | 1130 | 30.78 | yellow | 878 |
| C27 + Ir(2-phq)₃ | 6 | 1158 | 31.63 | yellow | 888 |
| C39 + Ir(2-phq)₃ | 6 | 988 | 20.81 | yellow | 709 |
| C40 + Ir(2-phq)₃ | 6 | 1310 | 36.22 | yellow | 984 |
| C58 + Ir(2-phq)₃ | 6 | 1078 | 30.58 | yellow | 869 |

From the above test report summary of the organic EL devices, it is evident that the organic compound of formula (1) or formula (2) used as the phosphorescent host material has better performance than the prior art material BAlq. The organic EL devices of the present invention using the organic compound of formula (1) or formula (2) as the phosphorescent host material to collocate with the dopant material Ir(piq)₃ or Ir(2-phq)₃ have superior luminance and current efficiency and extended half-life time under the same voltage.

To sum up, the present invention discloses an organic compound, which can be used as the phosphorescent host material, the fluorescent host material, or the fluorescent dopant material of the light emitting layer, or the electron transporting material in organic EL devices. The mentioned organic compound is represented by the following formula (1) or formula (2):

formula (1)

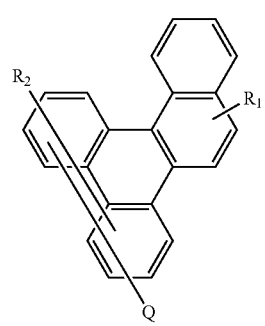

formula (2)

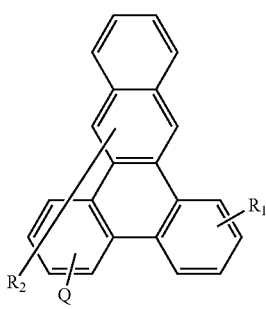

wherein Q is a group represented by formula (3) below:

formula (3)

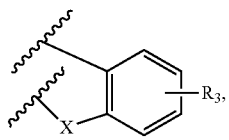

wherein X is a divalent bridge selected from the group consisting of O, S, $NR_4$, $CR_5R_6$, and $SiR_7R_8$; $R_1$ to $R_3$ are independently absent, a hydrogen atom, a halogen, a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms; $R_4$ is a hydrogen atom, a halogen, a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms; and $R_5$ to $R_8$ are independently a hydrogen atom, a halogen, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, or a substituted or unsubstituted heteroaryl group having 3 to 30 carbon atoms.

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. An organic compound represented by one of the following formula (4) to formula (9) and formula (11) to formula (21):

formula (4)

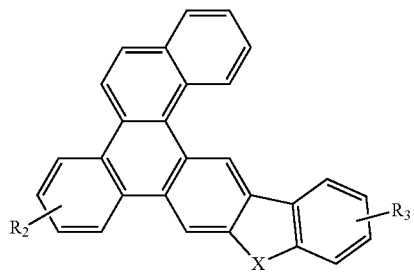

formula (5)

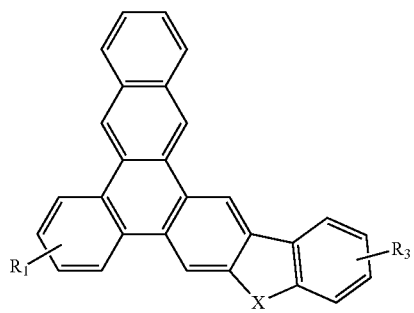

formula (6)

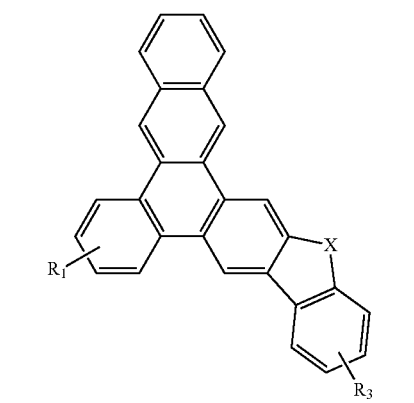

formula (7)

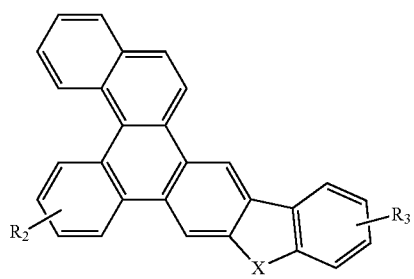

formula (8)

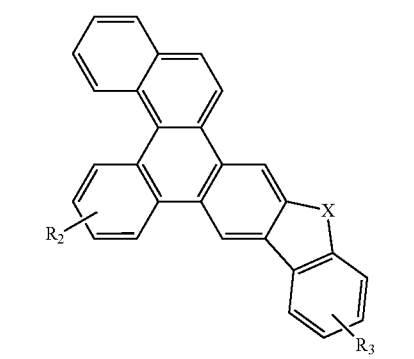

-continued
formula (9)
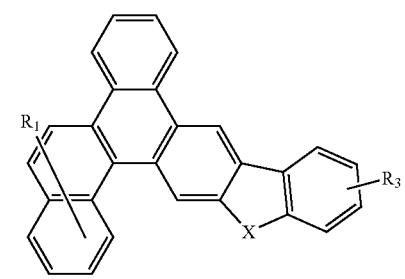
formula (11)
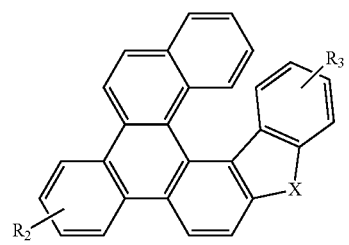
formula (12)
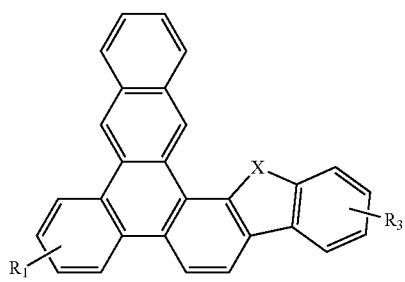
formula (13)
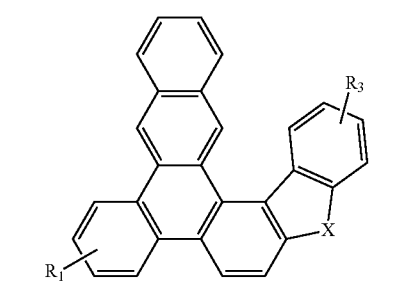
formula (14)
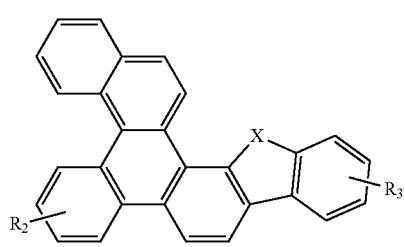
formula (15)
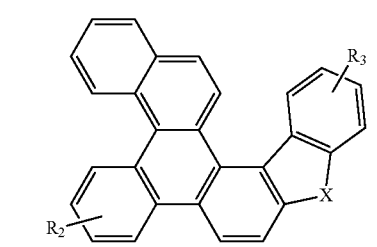
-continued
formula (16)
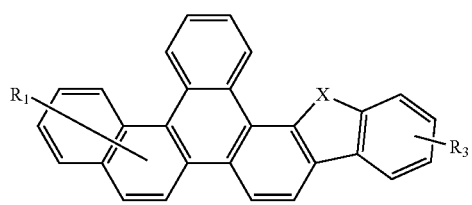
formula (17)
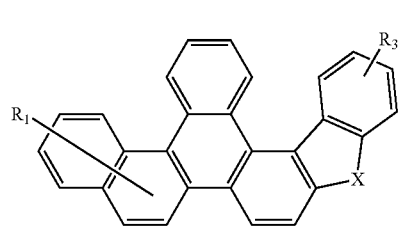
formula (18)
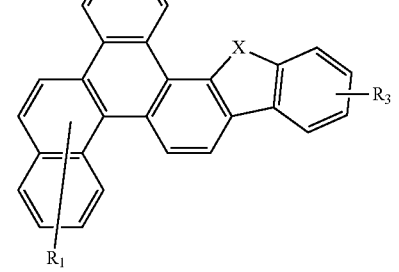
formula (19)
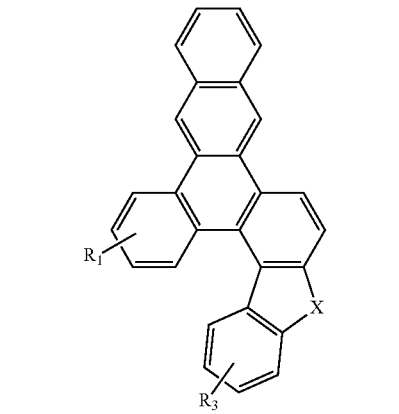
formula (20)
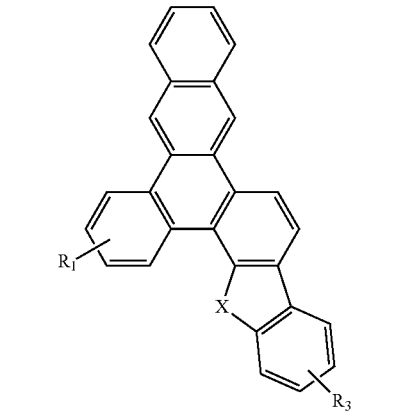

-continued

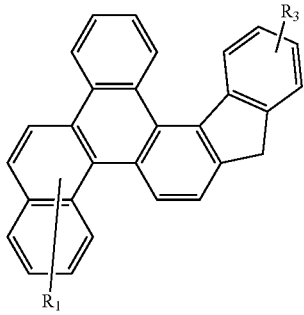

formula (21)

wherein X is a divalent bridge selected from the group consisting of O, S, $NR_4$, $CR_5R_6$, and $SiR_7R_8$; $R_1$ to $R_3$ are independently absent, a hydrogen atom, a halogen, a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms; $R_4$ is a hydrogen atom, a halogen, a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms; and $R_5$ to $R_8$ are independently a hydrogen atom, a halogen, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, or a substituted or unsubstituted heteroaryl group having 3 to 30 carbon atoms.

2. The organic compound according to claim 1, wherein the alkyl group, aralkyl group, aryl group, heteroaryl group, arylamine group, or heteroarylamine group is substituted by a halogen, an alkyl group, an aryl group, or a heteroaryl group.

3. The organic compound according to claim 1, wherein $R_1$ to $R_4$ are independently a substituted or unsubstituted phenyl group, a substituted or unsubstituted biphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted triphenylenyl group, a substituted or unsubstituted benzimidazole group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted diphenylphosphine oxide group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group, a substituted or unsubstituted dihydrophenazine group, a substituted or unsubstituted diphenylamine group, a substituted or unsubstituted triphenylamine group, a substituted or unsubstituted phenyldibenzofuranylamine group, or a substituted or unsubstituted phenyldibenzothiophenylamine group.

4. An organic compound of formula (1) or formula (2) below:

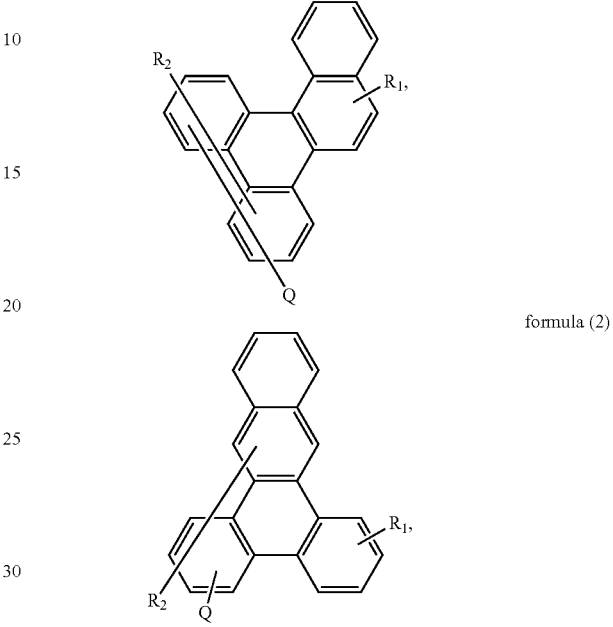

formula (1)

formula (2)

wherein Q is a group represented by formula (3) below:

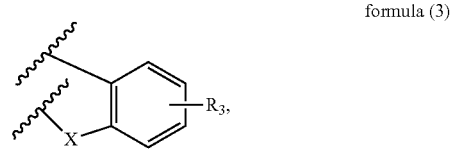

formula (3)

wherein X is a divalent bridge selected from the group consisting of O, S, $NR_4$, $CR_5R_6$, and $SiR_7R_8$; wherein $R_5$ to $R_8$ are independently a hydrogen atom, a halogen, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, or a substituted or unsubstituted heteroaryl group having 3 to 30 carbon atoms; and wherein $R_1$ to $R_4$ independently represent one of the following substituents:

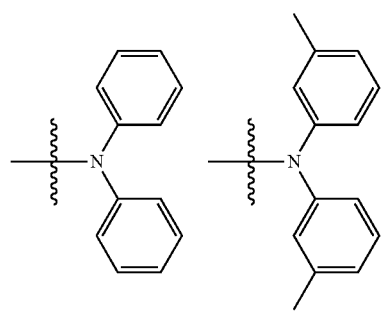

-continued
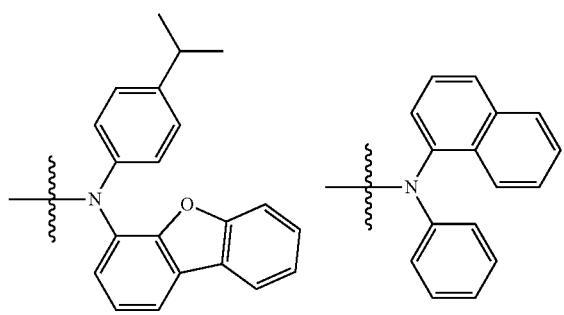
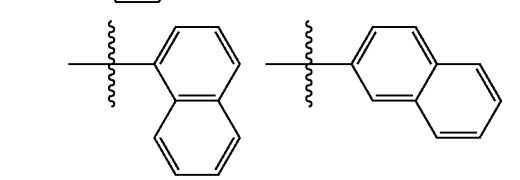
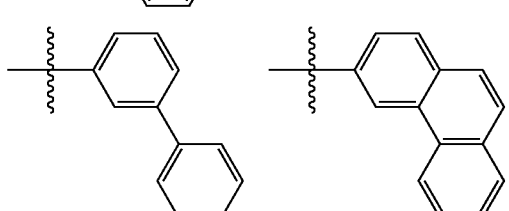
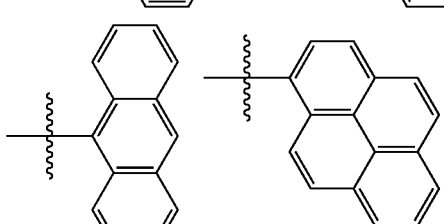
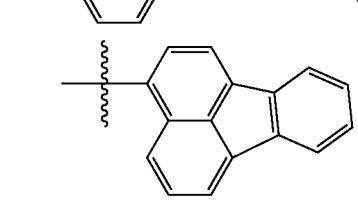
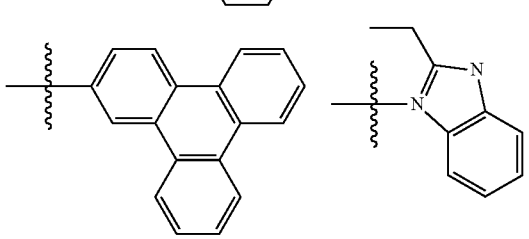
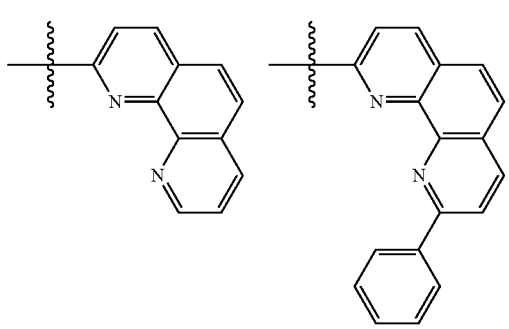
-continued
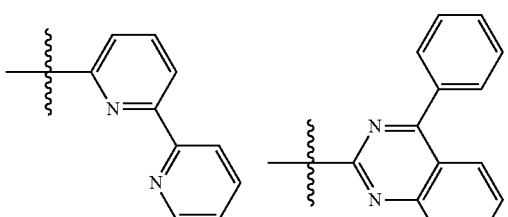
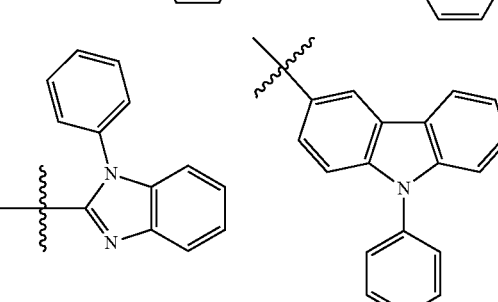
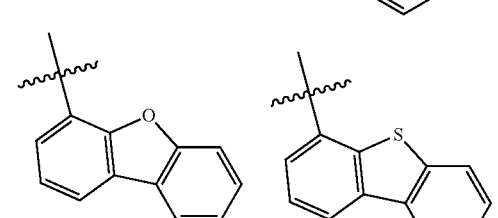
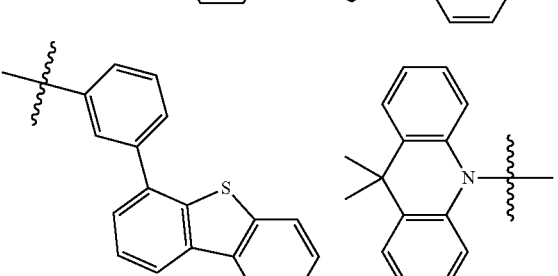
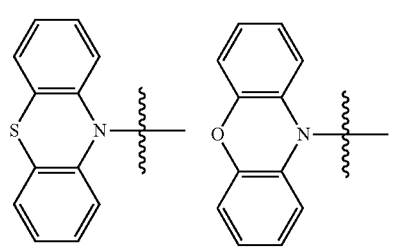
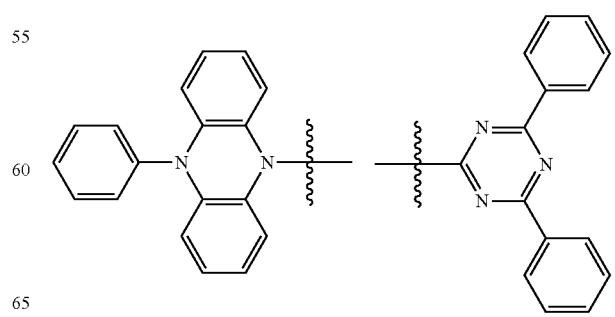

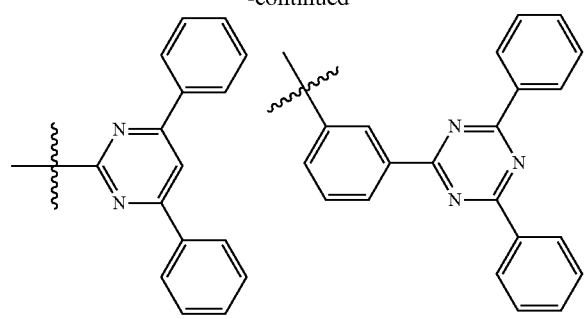
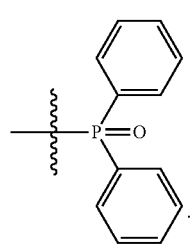
5. An organic compound, wherein the organic compound is one of the following compounds:
C1
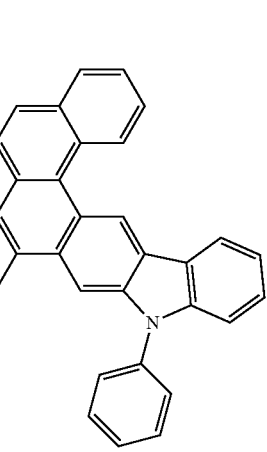
C2
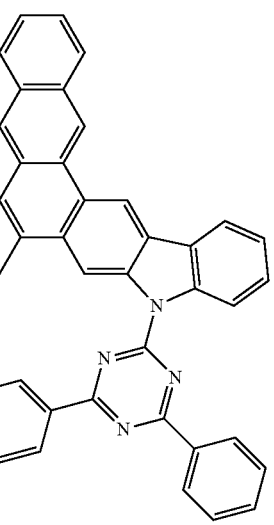
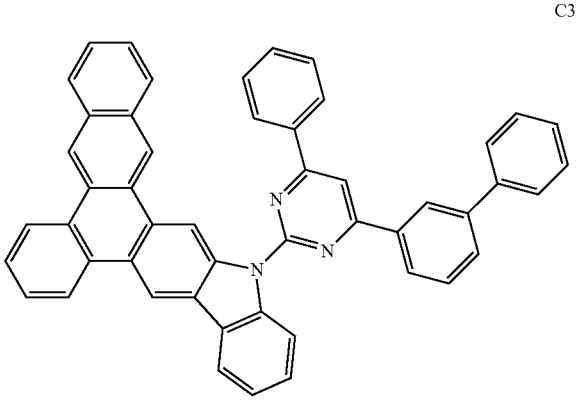
C3
C4
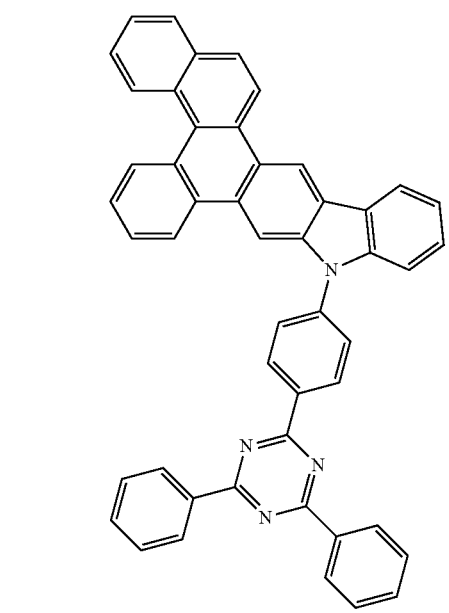
C5
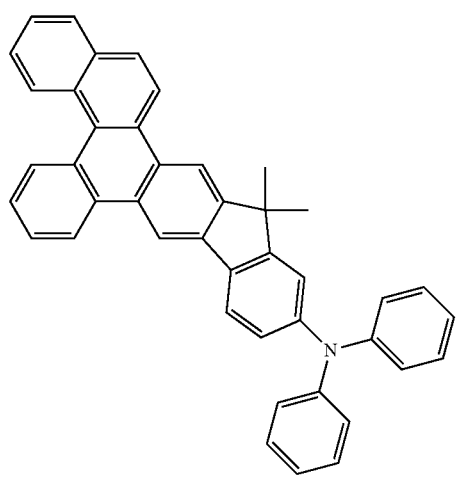

C6
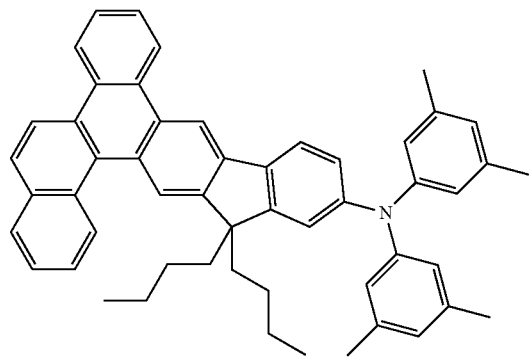
C7
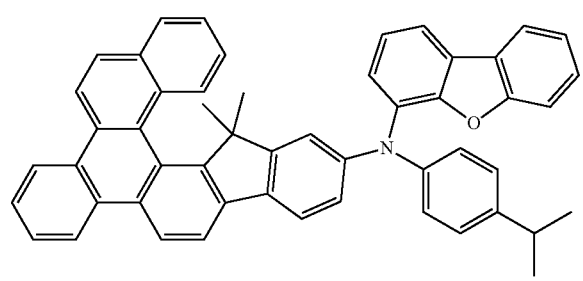
C8
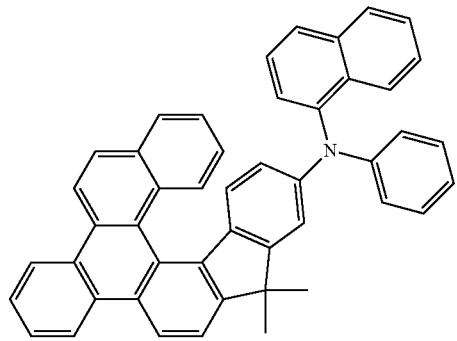
C9
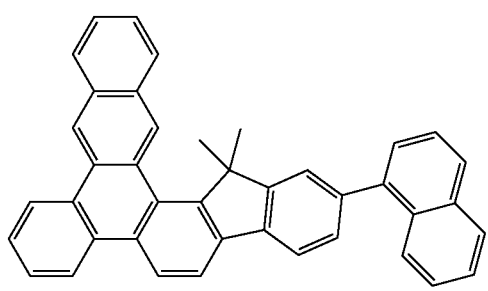
C10
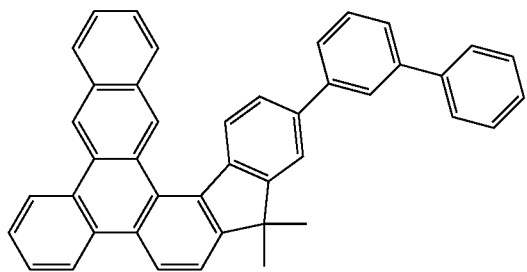
C11
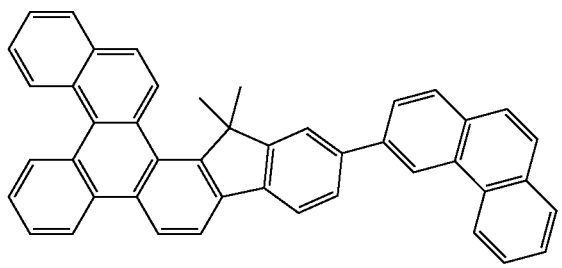
C12
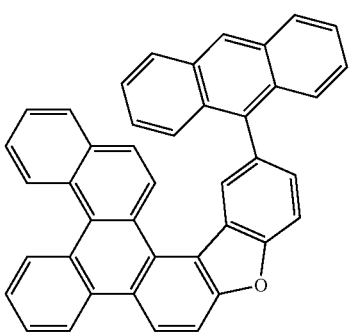
C13
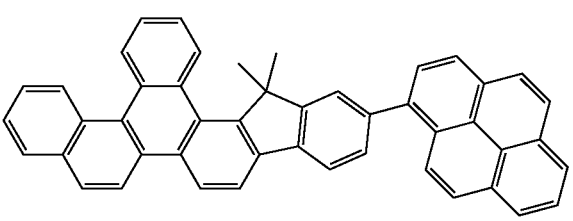
C14
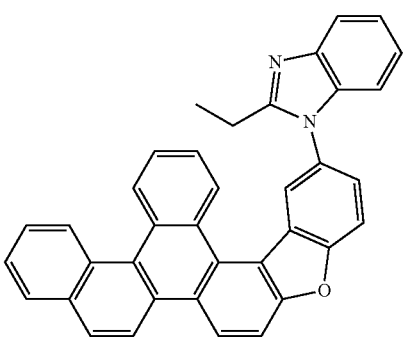
C15
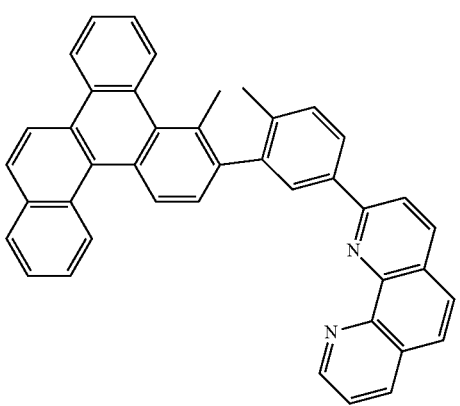

-continued
C16
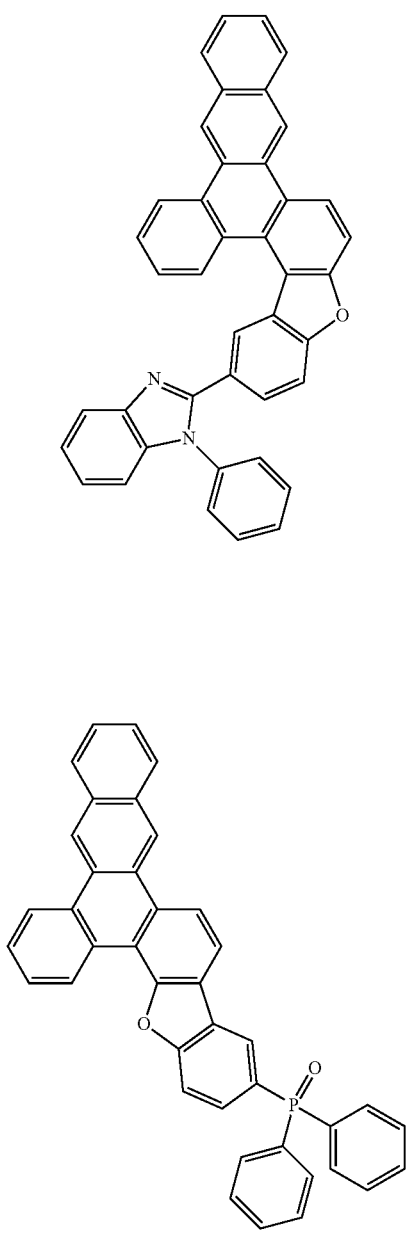
C17
C18
C19
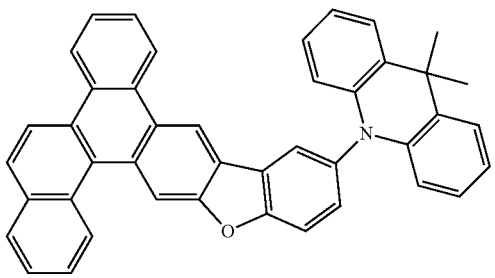
C20
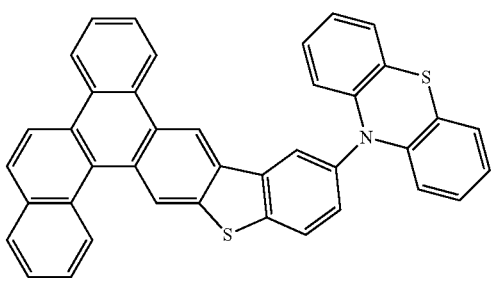
C21
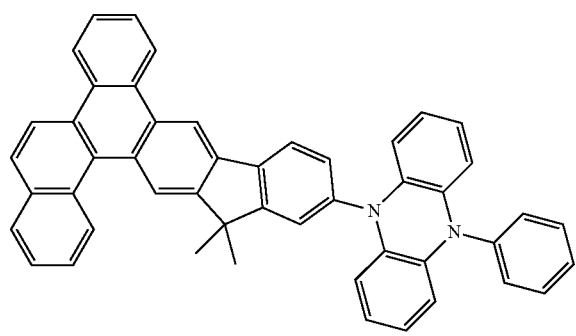
C22
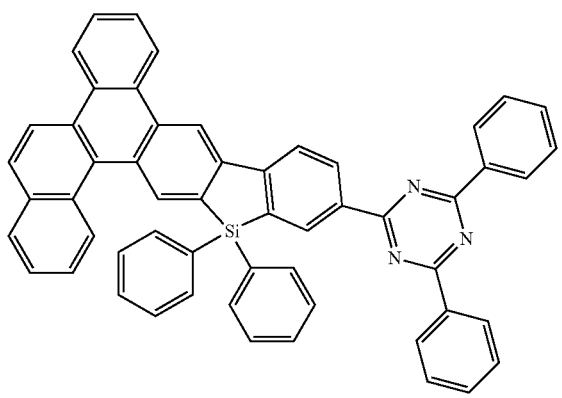

C23
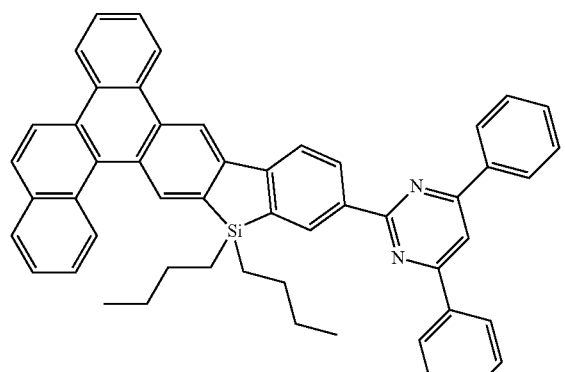
C24
C25
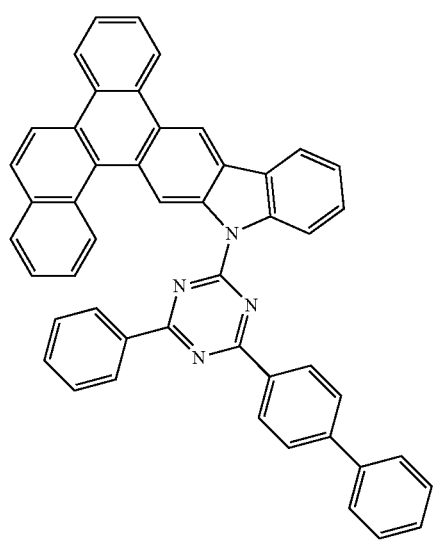
C26
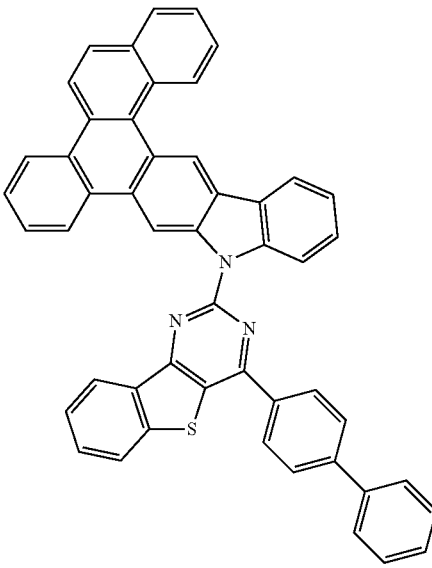
C27
C28
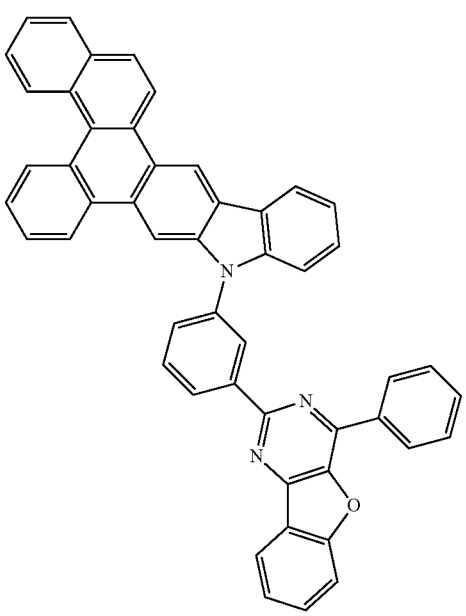

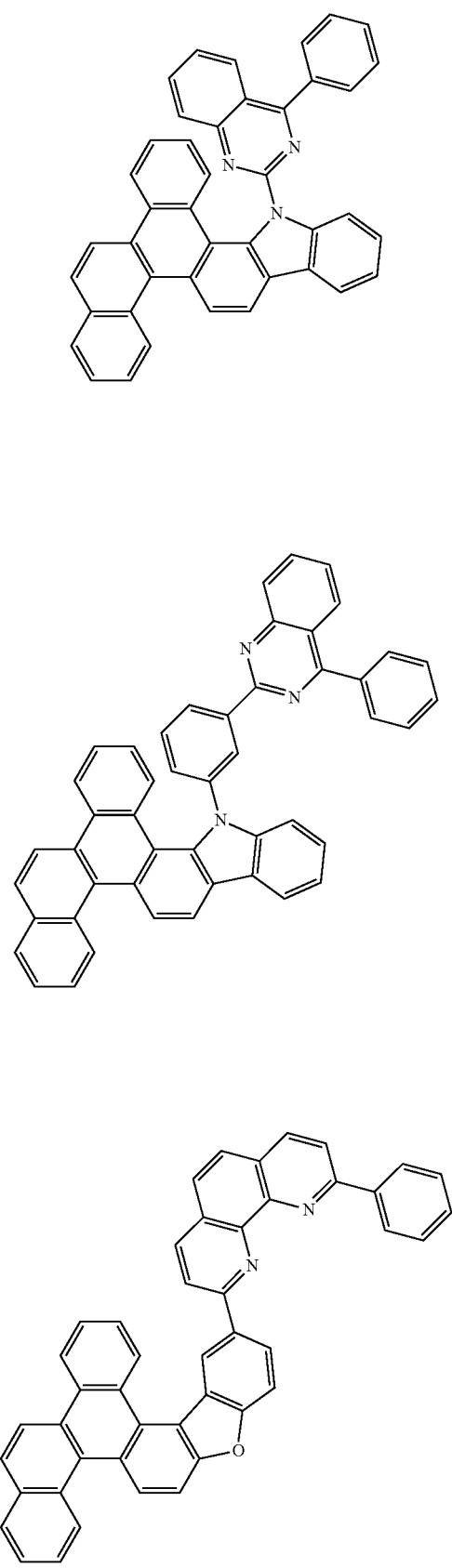
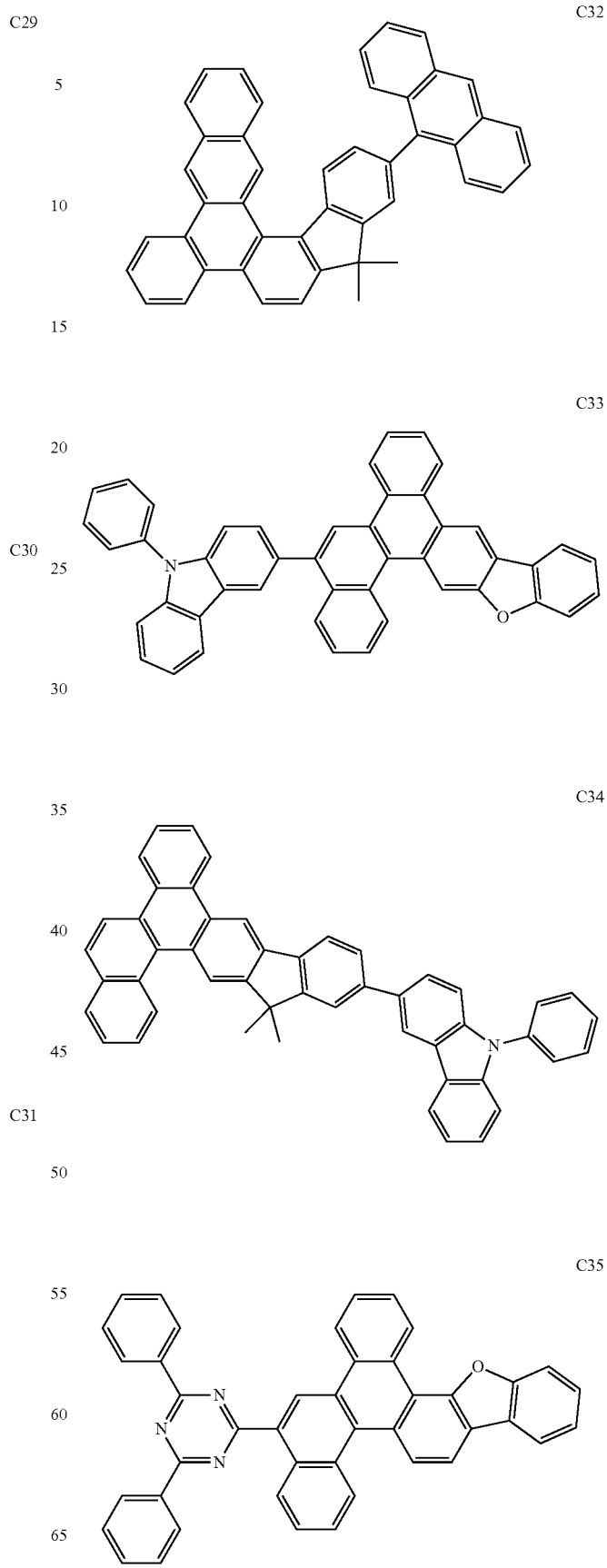

C36
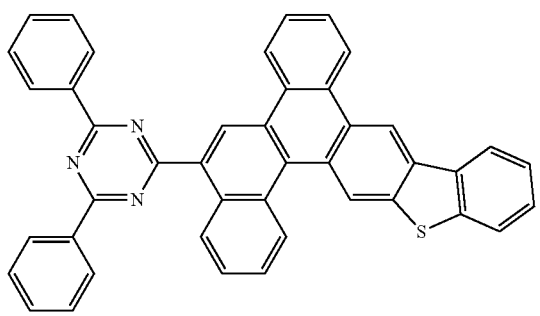
C37
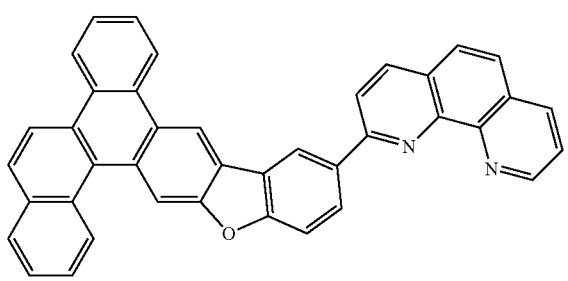
C38
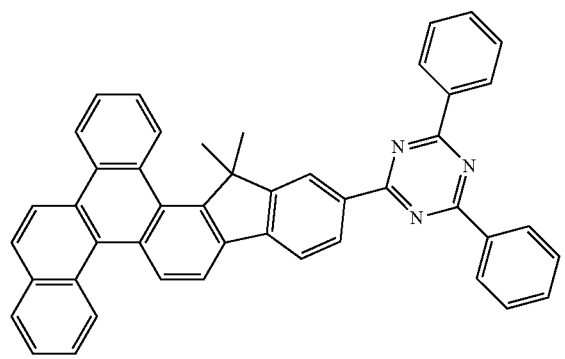
C39
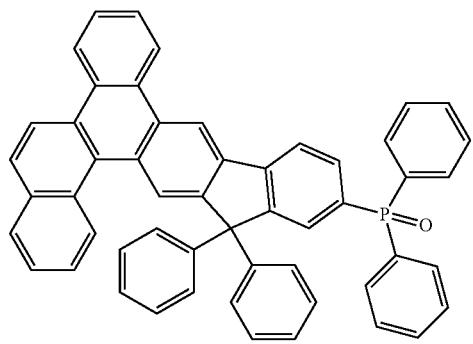
C40
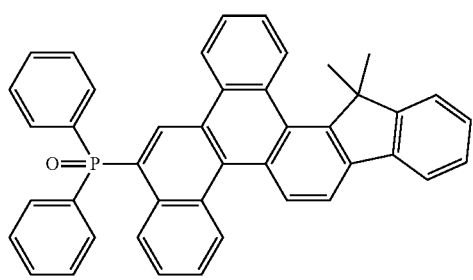
C41
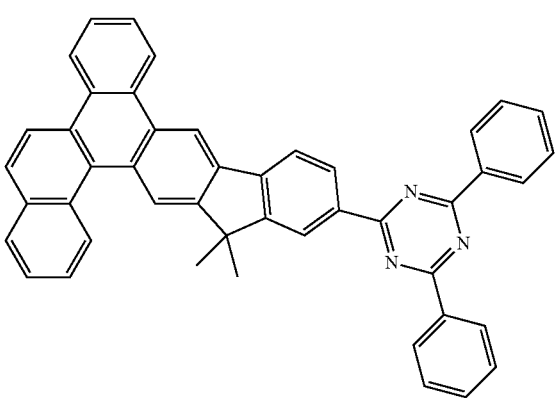
C42
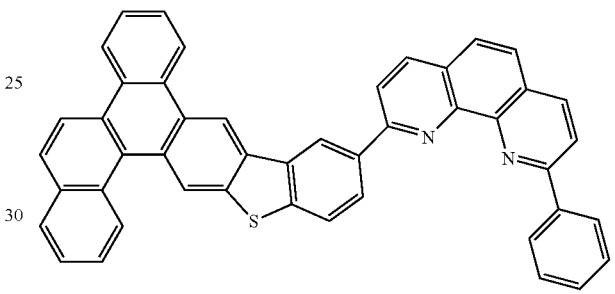
C43
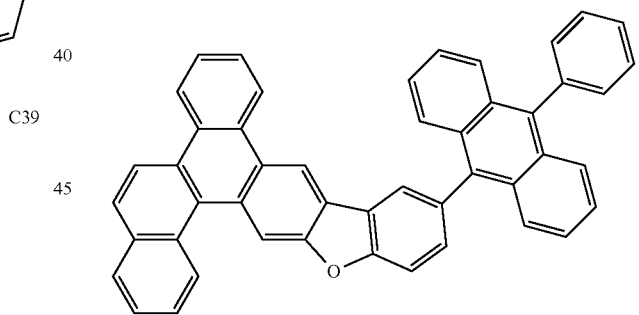
C44
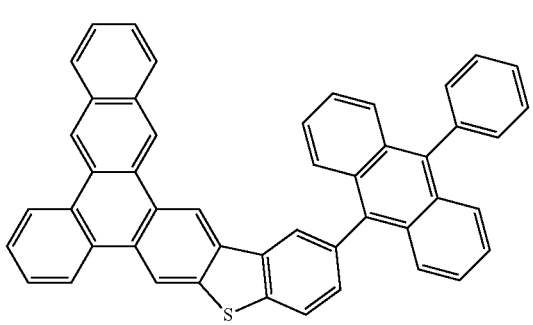

C45
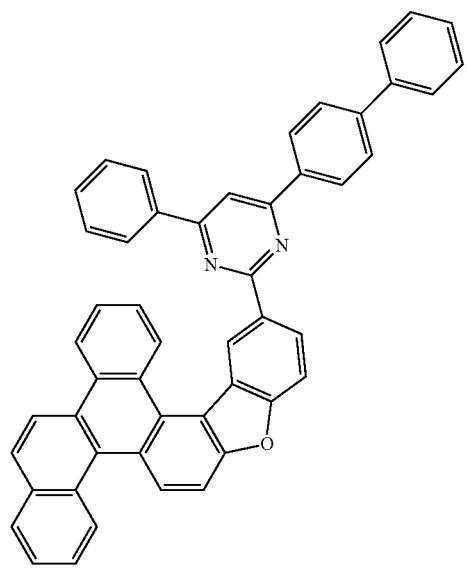
C46
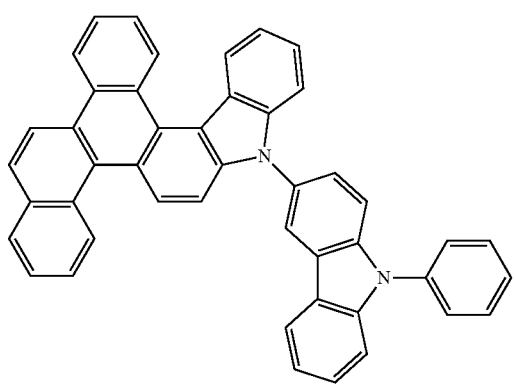
C47
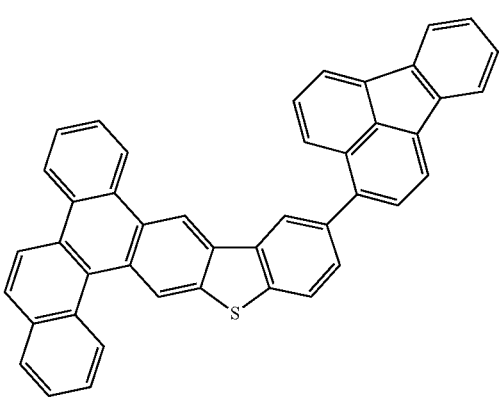
C48
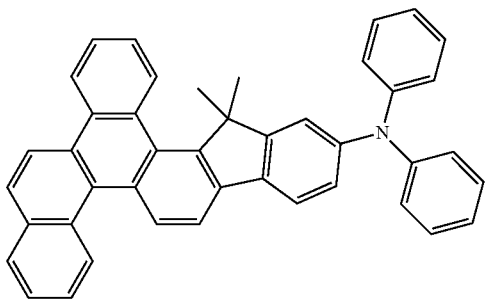
C49
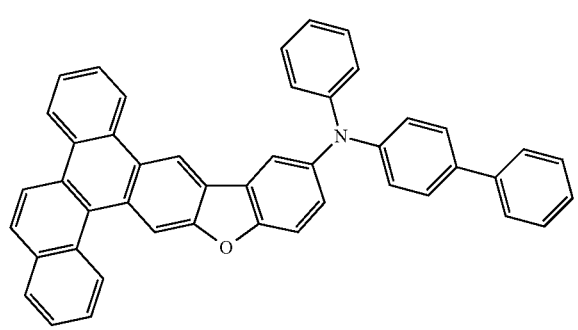
C50
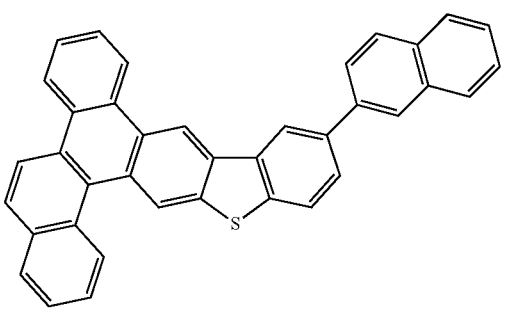
C51

-continued
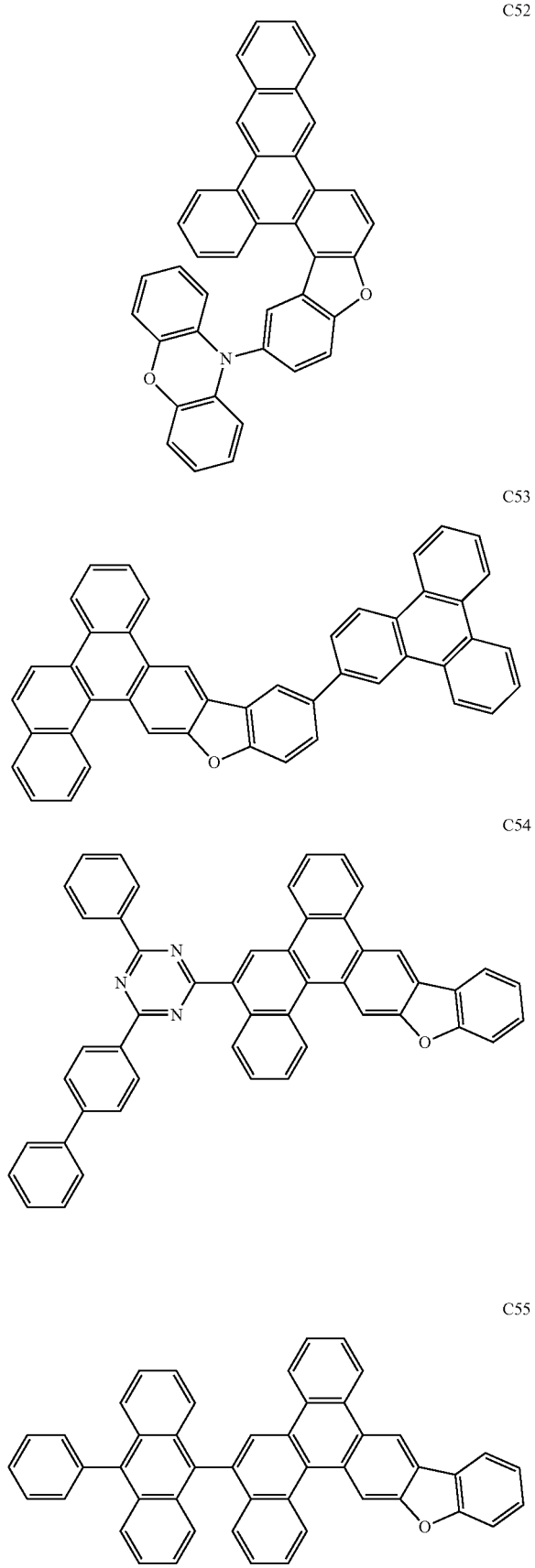
-continued
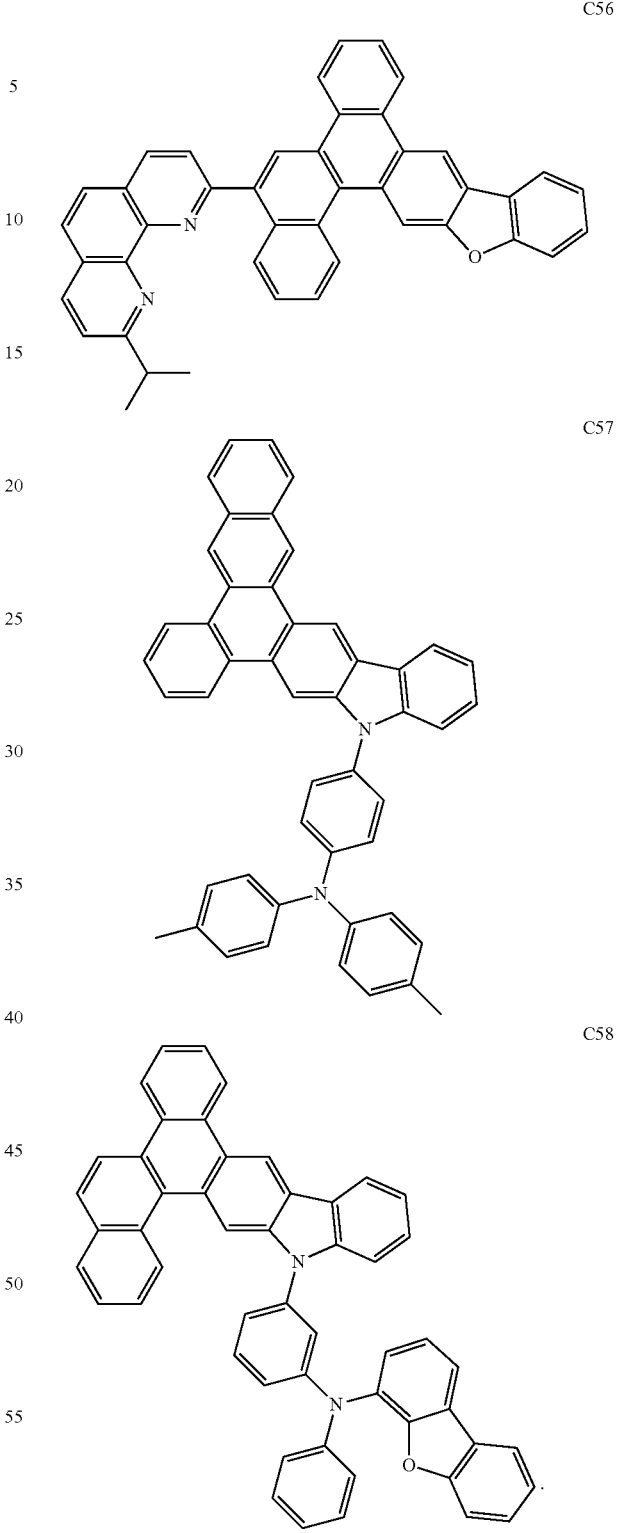
6. An organic electroluminescence device, comprising a pair of electrodes composed of a cathode and an anode, and a light emitting layer and one or more organic thin film layers between the pair of electrodes, wherein at least one of the light emitting layer and the organic thin film layer comprises the organic compound of claim 1.

7. The organic electroluminescence device according to claim 6, wherein the light emitting layer comprising the organic compound of one of the following formula (4) to formula (9) and formula (11) to formula (21) is a host material.

8. The organic electroluminescence device according to claim 6, wherein the light emitting layer comprising the organic compound of one of the following formula (4) to formula (9) and formula (11) to formula (21) is a fluorescent dopant material.

9. The organic electroluminescence device according to claim 6, wherein the organic thin film layer comprising the organic compound of one of the following formula (4) to formula (9) and formula (11) to formula (21) is an electron transporting layer.

10. The organic electroluminescence device according to claim 6, wherein the organic electroluminescence device is a lighting panel.

11. The organic electroluminescence device according to claim 6, wherein the organic electroluminescence device is a backlight panel.

* * * * *